US012753215B2

(12) United States Patent
Mo

(10) Patent No.: US 12,753,215 B2
(45) Date of Patent: Oct. 6, 2026

(54) ß-AMYLOID CYCLIC RIBONUCLEIC ACID, POLYPEPTIDE, AND APPLICATION THEREOF

(71) Applicant: Dingding Mo, Zhongshan City (CN)

(72) Inventor: Dingding Mo, Zhongshan City (CN)

( * ) Notice: Subject to any disclaimer, the term of this patent is extended or adjusted under 35 U.S.C. 154(b) by 1268 days.

(21) Appl. No.: 17/627,991

(22) PCT Filed: Jul. 19, 2019

(86) PCT No.: PCT/CN2019/096755
§ 371 (c)(1),
(2) Date: Jan. 18, 2022

(87) PCT Pub. No.: WO2021/012082
PCT Pub. Date: Jan. 28, 2021

(65) Prior Publication Data

US 2022/0275037 A1 Sep. 1, 2022

(51) Int. Cl.
*C07K 14/47* (2006.01)
*C07K 16/18* (2006.01)
*C12N 15/113* (2010.01)
*G01N 33/50* (2006.01)
*G01N 33/68* (2006.01)

(52) U.S. Cl.
CPC .......... *C07K 14/4711* (2013.01); *C07K 16/18* (2013.01); *C12N 15/113* (2013.01); *G01N 33/5088* (2013.01); *G01N 33/6896* (2013.01); *C12N 2310/11* (2013.01); *G01N 2800/2821* (2013.01); *G01N 2800/52* (2013.01)

(58) Field of Classification Search
CPC .......................... C12N 15/113; C12N 2310/11
See application file for complete search history.

(56) References Cited

U.S. PATENT DOCUMENTS

2020/0339991 A1* 10/2020 Milstein ............... C12N 15/113

FOREIGN PATENT DOCUMENTS

CN 108342468 A 7/2018
WO 2017055487 A2 4/2017

OTHER PUBLICATIONS

Graham, W. V., Bonito-Oliva, A., & Sakmar, T. P. (2017). Update on Alzheimer's disease therapy and prevention strategies. Annual review of medicine, 68(1), 413-430. (Year: 2017).*

Galvin, J. E. (2017). Prevention of Alzheimer's disease: lessons learned and applied. Journal of the American Geriatrics Society, 65 (10), 2128-2133. (Year: 2017).*

Mo, Dingding et al., "The role of Aß circRNA in Alzheimer's disease: alternative mechanism of Aß biogenesis from Aß circRNA translation", BioRxiv, Jul. 11, 2018; 22 pgs.

Mo, Dingding; "The role of Aß circRNA in Alzheimer's disease"; BioRxiv, Feb. 6, 2018; 15 pgs.

circBase. "hsa_ circ_0007556 " circBase, Dec. 31, 2017; 2 pgs.

circBase. "hsa_ circ_0115725 " circBase, Dec. 31, 2017; 1 pg.

Shi, Zhemin et al.; "The circular RNA ciRS-7 promotes APP and BACE1 degradation in an NF-KB- dependent manner"; The FEBS Journal, vol. 284, Dec. 31, 2017; pp. 1096-1109.

Idda, M. Laura, et al.; "Noncoding RNAs in Alzheimer's disease"; WIREs RNA, vol. 9, Dec. 31, 2018; e1463; 13 pgs.

International Search Report and Written Opinion issued in International Application No. PCT/CN2019/096755; Apr. 17, 2020; 20 pgs.

Mo, Dingding et al.; "The role of Aß circRNA in Alzheimer's disease: alternative mechanism of Aß biogenesis from Aß circRNA translation"; BioRxiv, Sep. 5, 2018; 20 pgs.

* cited by examiner

*Primary Examiner* — Jennifer Dunston
*Assistant Examiner* — Christina Tran
(74) *Attorney, Agent, or Firm* — HAUPTMAN HAM, LLP

(57) ABSTRACT

The invention discloses a β-amyloid cyclic ribonucleic acid, a polypeptide and an application thereof. The present invention finds that the APP gene can generate a variety of circular RNAs from the Aβ coding region through reverse splicing, which is named β-amyloid circular ribonucleic acid circAβ. With the help of the newly established circular RNA research method, a variety of peptides produced by circAβ were identified, and such peptides could be further processed to form Aβ, which in turn formed β-amyloid plaques in primary neuronal cultures, reflecting key hallmarks of AD neuropathology. circAβ and its translated proteins represent novel targets in AD therapy.

2 Claims, 12 Drawing Sheets

Figure 1A:
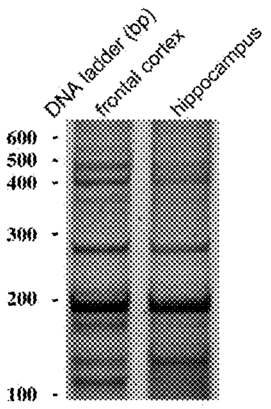

Specification includes a Sequence Listing.

>circAβ-a-DP, Aβ175

```
1                                                 50
miseprisygndalmpsltetkttvellpvngefslddlqpwhsfgadsv
51                                        ↓β      100
pantenevepvdarpaadrglttrpgsgltnikteeisevkmdaefrhds        SEQ ID NO: 92
101     ↓α         Aβ42            ↓γ             150
gyevhhqklvffaedvgsnkgaiiglmvggvviatvivitlvmlkkkqyt
151                    175
sihhgvveMSCFRKSKTIQMTSWPT
```

ß-AMYLOID CYCLIC RIBONUCLEIC ACID, POLYPEPTIDE, AND APPLICATION THEREOF

RELATED APPLICATIONS

The present application is a U.S. National Phase of International Application Number PCT/CN2019/096755 filed Jul. 19, 2019.

INCORPORATION BY REFERENCE

The sequence listing provided in the file entitled trans-NSequence-2026_05_18_mod.txt, which is an ASCII text file that was created on May 18, 2026, and which comprises 47,382 bytes, is hereby incorporated by reference in its entirety.

TECHNICAL FIELD

The present invention relates to the field of β-amyloid (Aβ), in particularly to β-amyloid cyclic ribonucleic acid (circAβ) and polypeptides produced from them; and the using in the prevention, diagnosis and treatment of Alzheimer's disease.

BACKGROUND TECHNIQUE

Alzheimer's disease (AD) is one of the most common dementias, accounting for approximately 70%. AD is a neurodegenerative disease characterized by decreased memory ability and progressive cognitive dysfunction. As a disease related to aging, the biggest known risk factor for Alzheimer's disease is increasing age. The cause of Alzheimer's disease is the accumulation of β-amyloid peptide (Aβ) and the hyperphosphorylation of tau protein. It has been proven that mutations in APP (β-amyloid precursor protein) and presenilin genes (involved in P proteolytic processing of APP protein) accelerate the accumulation of Aβ polypeptides. The polymerization of Aβ leads to toxic oligomers, which in turn aggregate into insoluble β-amyloid plaques (AB plaques). This process eventually leads to hyperphosphorylation of tau protein. It then forms neurofibrillary tangles in neurons, triggering complex downstream reactions, and ultimately leading to neuronal death. This neurodegenerative pathology due to genetic mutations is called familial Alzheimer's disease. The role of various mutations in familial Alzheimer's disease has been clearly studied; however, this familial Alzheimer's disease accounts for less than 1-5% of all cases. The most common form of Alzheimer's disease is "sporadic". This type of Alzheimer's disease is common in patients 65 years of age or older, and the underlying genetic or molecular cause is still unknown. Although there are potential genetic differences between familial and sporadic forms of Alzheimer's disease, the two disease subtypes share overlaps in various pathophysiological relevant aspects of disease development. However, it has been found that in clinical studies that most patients with Alzheimer's disease do not have mutations in APP and related genes. At the same time, overexpression of normal APP protein in the mouse brain does not produce significant AB plaques. These studies indicate that Aβ produced by APP proteolysis is not the most important source of Aβ. Therefore, where the most critical and pathogenic AB comes from is still a largely unknown. Finding the source of Aβ is the key to diagnosis, prevention, and treatment of Alzheimer's disease.

SUMMARY OF THE INVENTION

After in-depth research, the inventor found that APP, a key gene for Alzheimer's disease, can synthesize circular RNA related to AB (named β-amyloid cyclic ribonucleic acid, circAβ) in the human brain, and be translated and processed into the Aβ polypeptide, the key fatal factor of Alzheimer's disease, and forms Aβ plaques in neuronal cultures, indicating that the Aβ encoded by circAβ has important pathogenic potential. Since the transcription and translation of circAβ do not require mutations in the APP gene, the neurotoxic AB encoded by circAβ can perfectly explain why the normal population also develops Alzheimer's disease with aging. The present invention has been completed based at least in part on this discovery.

The present invention not only reveals the new and most important Aβ production pathway in normal humans, but also provides a new mechanism for the pathogenesis of Alzheimer's disease, and provides future diagnosis, prevention, and treatment of the disease with a brand-new target.

DESCRIPTION OF THE FIGURES AND DRAWINGS

FIGS. 1A-1I Identification of circAβ in human brain and its overexpression in HEK293 cells.

Figure 1B:
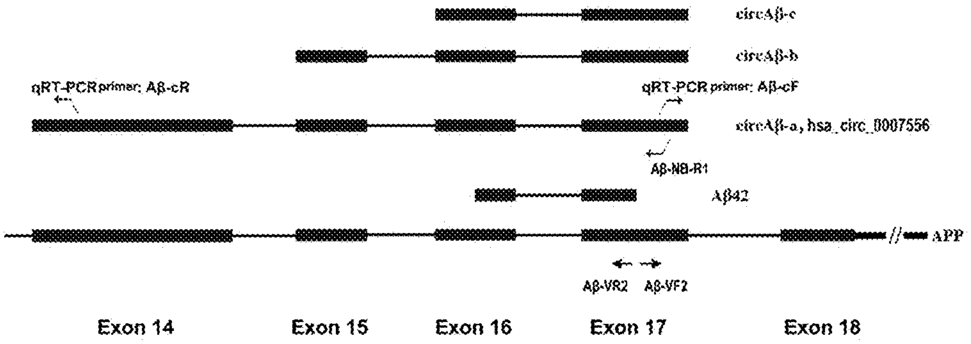
Figure 1C:
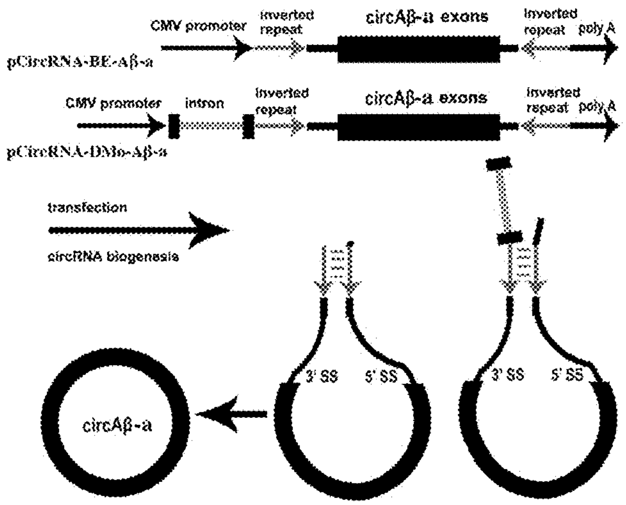
Figure 1D:
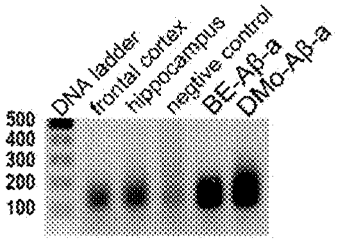
Figure 1E:
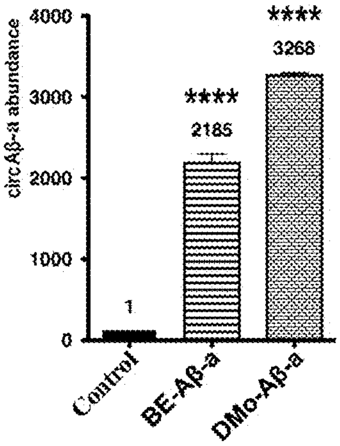
Figure 1F:
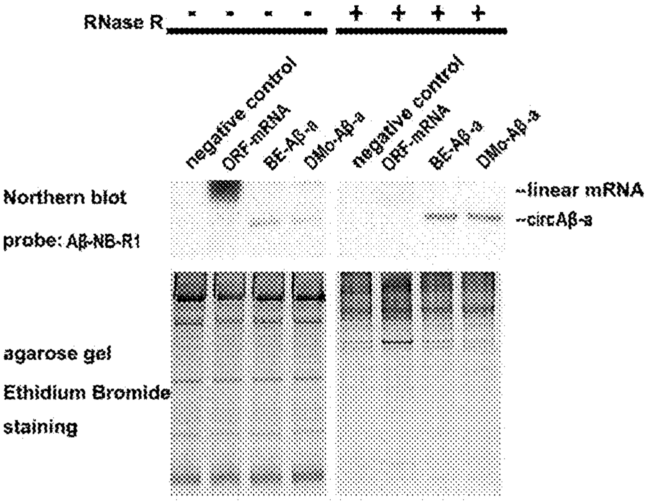

FIG. 1A. 5% natural polyacrylamide gel electrophoresis circAβ RT-PCR product, which has a reverse primer (Aβ-VF2, Aβ-VR2) located in exon 17 of the human APP gene in a human brain sample; Two human brain RNA samples are used. FIG. 1B. Location of circAβ-a, b, c, d in APP gene; Aβ42 sequence is used as a position reference.—hsa_circ_0007556 is named circAβ-a in this study. The amyloid-β (Aβ) sequence is in exons 16 and 17; Aβ-cF and Aβ-cR are used to amplify circAβ-a by qRT-PCR. FIG. 1C. circAβ-a overexpression construct. FIG. 1D. RT-PCR verification of circAβ-a expression in human brain samples (frontal lobe and hippocampus) and HEK293 cells overexpressing circAβ-a; control, pCircRNA-DMo empty vector transfected HEK293; BE-CircAβ-a, pCircRNA-BE-Aβ-a was transfected into HEK293; DMo-circAβ-a, pCircRNA-DMo-Aβ-a were transfected into HEK293; RT-PCR verification of circAβ-a by another set of oligonucleotides is shown in Table 1. FIG. 1E. Quantification of circAβ-a expression in HEK293 cells; control, empty vector (pCircRNA-DMo); BE-circAβ-a, pCircRNA-BE-Aβ-a, DMo-circAβ-a, pCircRNA-DMo-Aβ-a. All statistical T tests were compared with control samples, **, $P<0.0001$, $n=4$. FIG. 1F. Northern blot analysis of circAβ-a expression in HEK293 cells; ORF-mRNA, linear homologous ORF mRNA of circAβ-a. For RNase R treatment, 15 μg of total RNA was digested with 10 units of RNase R at 37° C. for 1 hour; − means no digestion; + means digestion; OligoAβ-NB-R1 (CCCACCATGAGTCCAATGATTGCACCTT-TGTTTGAACCCAC ATCTTCTGCAAAGAACACC, SEQ ID NO: 60) was used for northern blotting; agarose coagulation Ethidium bromide staining of the gel was used as a loading control. FIG. 1**G. Agarose gel electrophoresis of RT-PCR products (503 bp) using primers Aβ-VR2 and Aβ-VF2.

Figure 1G:
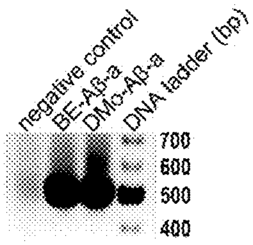
Figure 1H:
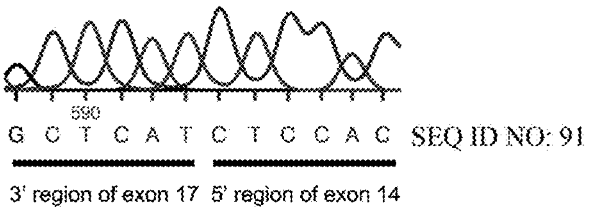
Figure 1I:
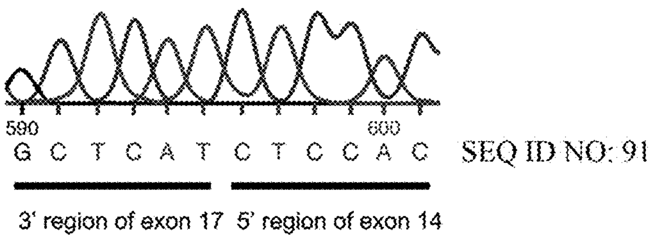

FIGS. 1H and 1I. Sequencing and comparison of RT-PCR products confirmed that circAβ-a is the same and contains exons 14, 15, 16 and 17 of APP gene without introns (data not shown); circAβ Sequencing—the junction region from the reverse splicing of pCircRNA-BE-Aβ-a and pCircRNA-DMo-Aβ-a.

Figure 2A:
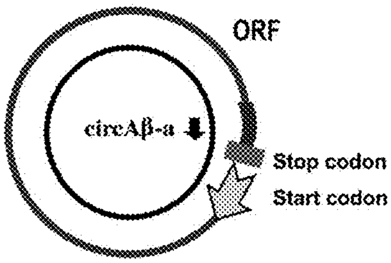
Figure 2B:
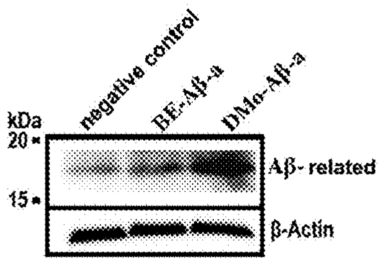
Figures 2C, 2D:
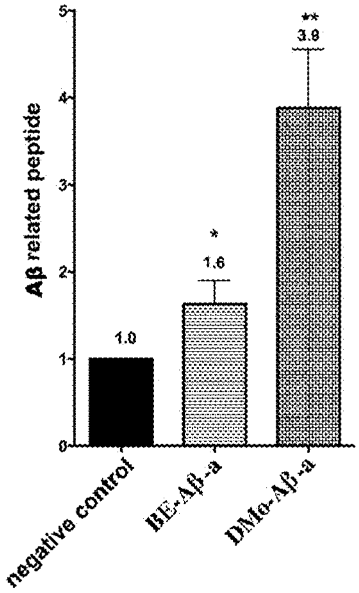
Figure 2E:
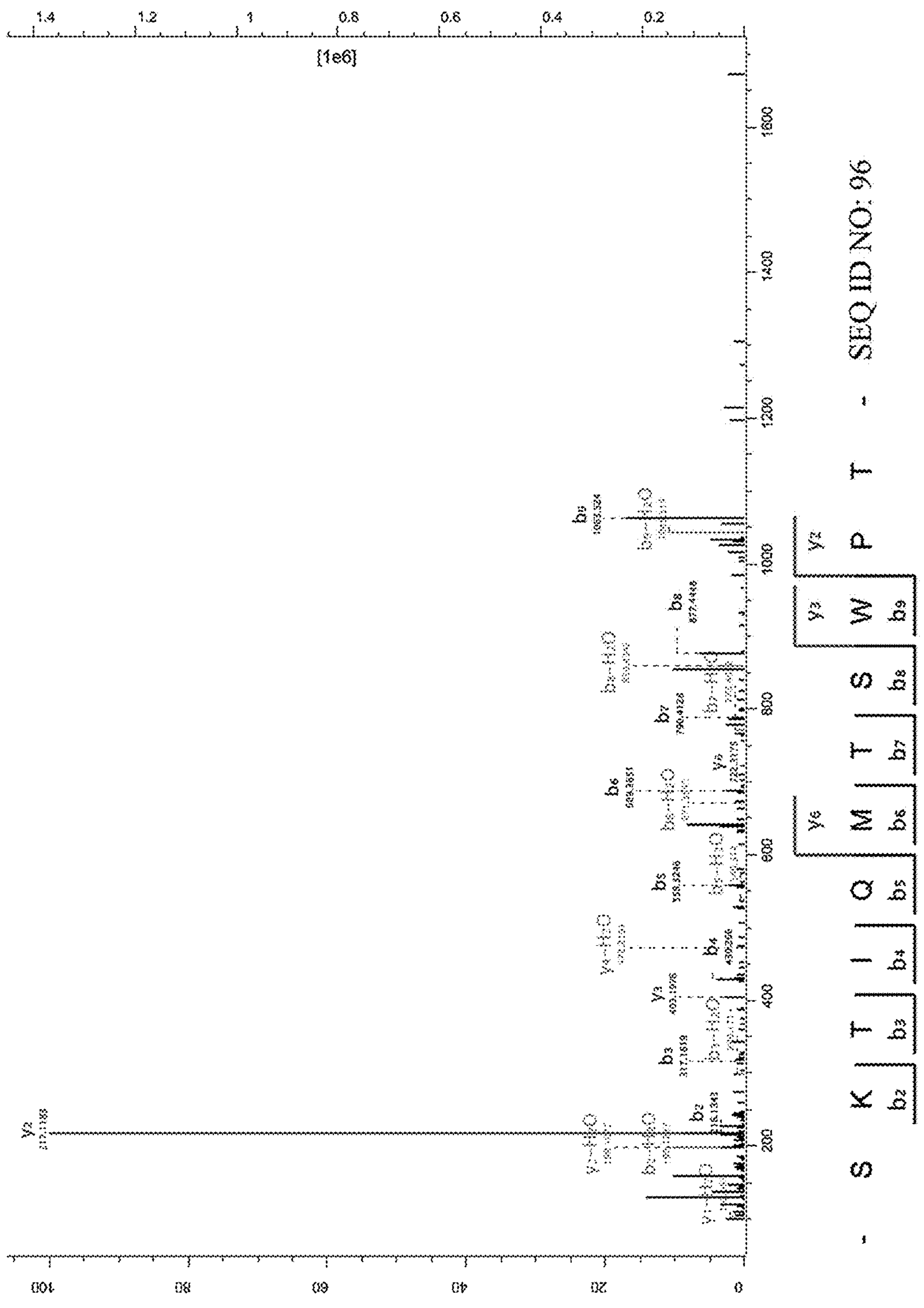

FIGS. 2A-2E circAβ-a is translated into Aβ-related peptides in HEK293 cells. FIG. 2A. The open reading frame (ORF) of circAβ-a is represented by the outer circle; the dark gray area, the unique peptide region of a protein translated by circAβ-a; the gray arrow, the translation initiation codon; the gray rectangle, the stop Codon; the inner black arrow shows the beginning of circAβ-a. FIG. 2B. Western blot of Aβ-related peptides in HEK293 cells; control, empty vector (pCircRNA-DMo); BE-Aβ-a, pCircRNA-BE-Aβ-a; DMo-Aβ-a, pCircRNA-DMoAβ-a; detection The obtained peptides are shown on the right: Aβ175, a circAβ-a-derived protein; β-actin is used as a loading control. FIG. 2C. Quantification of Aβ175 levels; all statistical T tests were performed on control samples; *, P≤0.05; **, P≤0.01; n≥3. FIG. 2D. The peptide sequence of Aβ175; black lowercase, the peptide sequence of Aβ175 is the same as the wild-type APP protein; α represents α-secretase; β represents β-secretase; γ represents γ-secretase; protease sites are indicated by arrows; The Aβ42 sequence is lowercase and underlined; the light uppercase indicates the unique peptide sequence of Aβ175; the light uppercase indicates the unique peptide detected by IP-MS. FIG. 2E. The mass spectrum of a unique peptide, which only exists in the circular translation of circAβ-a; the peptide was prepared by immunoprecipitation of Aβ175 with anti-Aβ antibody; the left ordinate is the relative intensity, and the right ordinate is the absolute intensity, horizontal The ordinate is m/z.

FIGS. 3A-3D. Overexpression of circAβ-a produces Aβ polypeptides and leads to the formation of Aβ plaques.

Figure 3A:
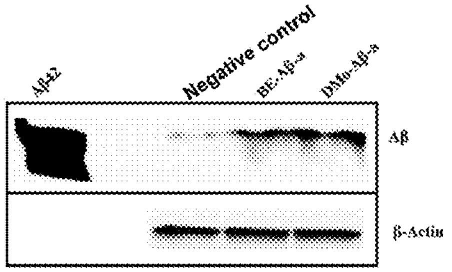
Figure 3B:
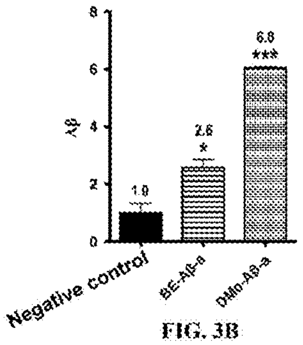
Figure 3C:
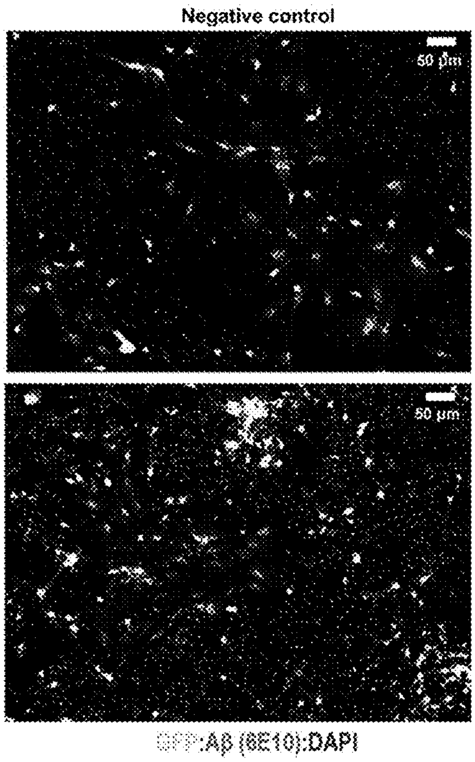
Figure 3D:
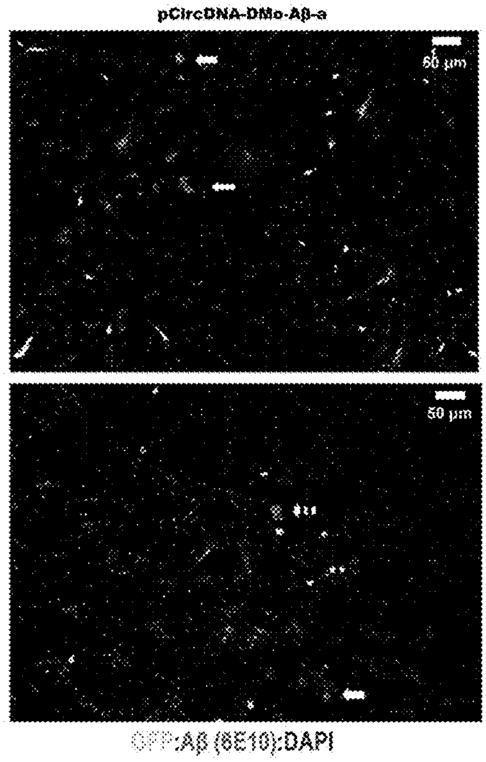

FIG. 3A. Western Blot Analysis of Immunoprecipitation (IP-WB) of Aβ polypeptide in the conditioned medium of circAβ-a overexpressing cells; HKE293 conditioned medium transfected with circAβ-a overexpression vector was treated with anti-Aβ antibody (6E10, 4G8; mouse antibody) immunoprecipitation; control, pCircRNA-DMo; BE-Aβ-a, pCircRNA-BE-Aβ-a; DMo-Aβ-a, pCircRNA-DMo-Aβ-a; Aβ antibody (D54D2, rabbit antibody) was used for Western blot; β-actin was used as a loading control. 5 ng of in vitro synthesized Aβ42 was used as an Aβ control in western blots. FIG. 3B. Quantification of A; all statistical T-tests performed compared to control samples; *, P≤0.05; ***, P≤0.001; n=3. FIG. 3C, FIG. 3D. circAβ-a overexpression produces Aβ plaques in mouse primary neuronal cultures; pCircRNA-DMo was used as an empty vector control. DMo-Aβ-a, pCircRNA-DMo-Aβ-a; GFP is shown in bright white; Aβ (6E10) is shown in light gray; brackets and white arrows indicate Aβ plaque locations; DAPI (nuclear staining) is shown in gray. Notably, the same number of starting neurons was used in each transfection; the different densities of neurons observed in the images between FIG. 3C and FIG. 3D may be caused by the toxicity of the Aβ peptide.

Figure 4:
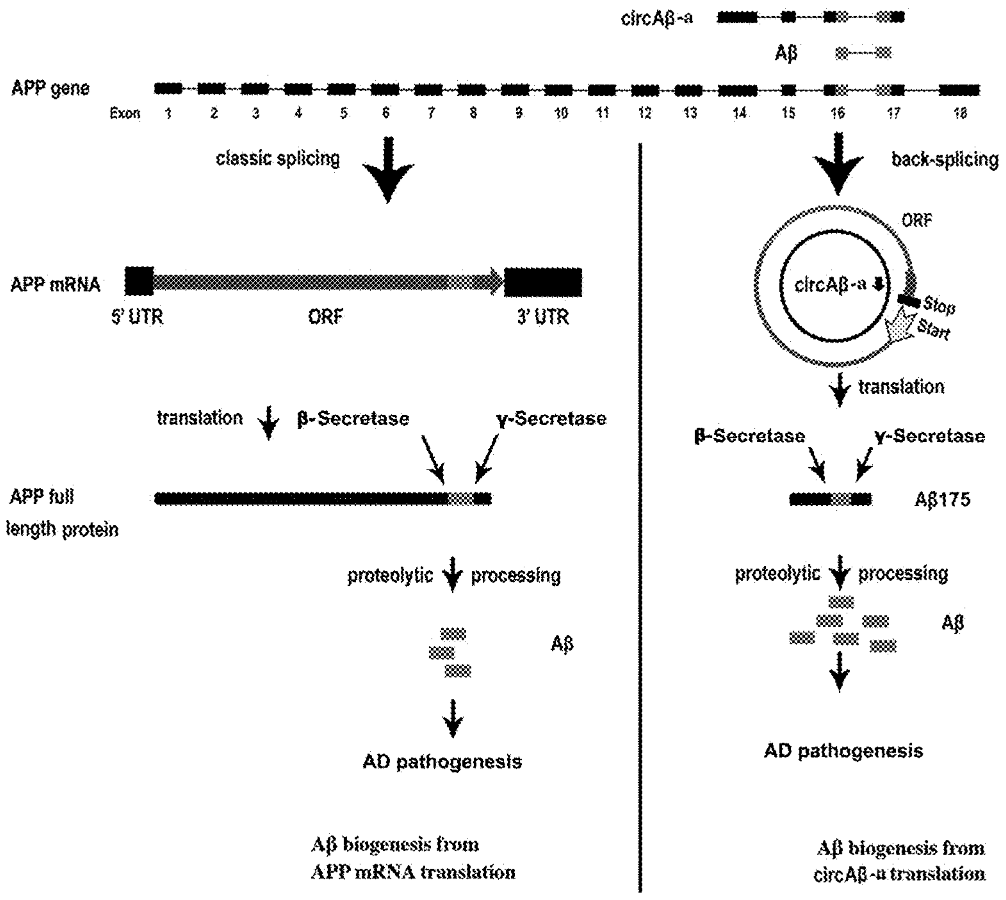

FIG. 4. Alternative pathways for Aβ production in Alzheimer's disease.

At the top, the exon sequences contained in the circAβ-a and Aβ polypeptides (light grey) are aligned with the full-length APP gene. On the left, linear APP mRNA transcribed from the APP gene undergoes canonical splicing and is then translated into the full-length APP protein. Proteolytic processing of the APP protein produces A [beta] polypeptides (Aβ40, Aβ42, light grey), which play a pathogenic role in AD pathology. On the right, circAβ-a is synthesized by back-splicing of the APP gene. Open reading frames (ORFs) are in grey, Aβ sequences are in light grey, start codons are light grey arrows and stop codons are black rectangles. Translation of circAβ-a produces an Aβ-related peptide (Aβ175), which is further processed to form AB.

Figure 5:
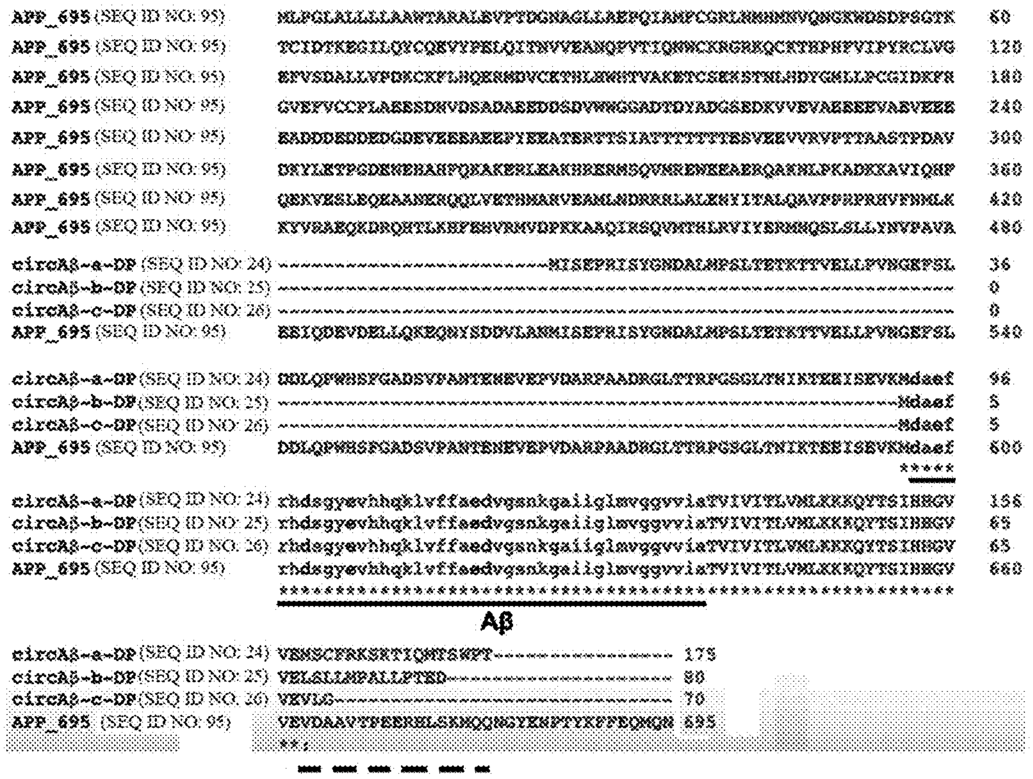

FIG. 5. Sequence alignment of circAβ-a-DP, circAβ-b-DP, circAβ-c-DP and APP_695 (SEQ ID NO: 95).

The solid line represents the sequence of AB; the dashed line represents the sequence-unique region (distinct from APP) of the circAβ expressed protein, named circAβ-DP-SP.

FIGS. 6A-6D. Expression identification of circAβ-a-derived peptides from human brain.

Figure 6A:
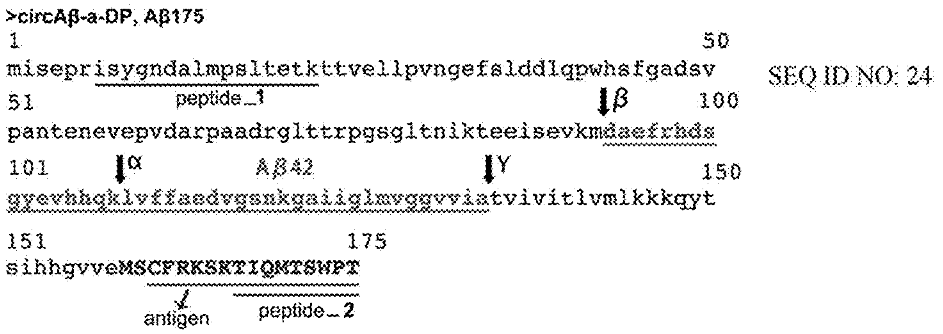
Figure 6B:
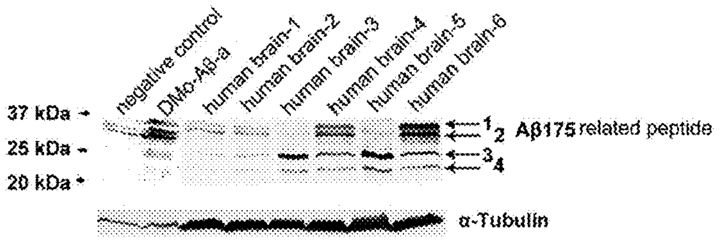
Figure 6C:
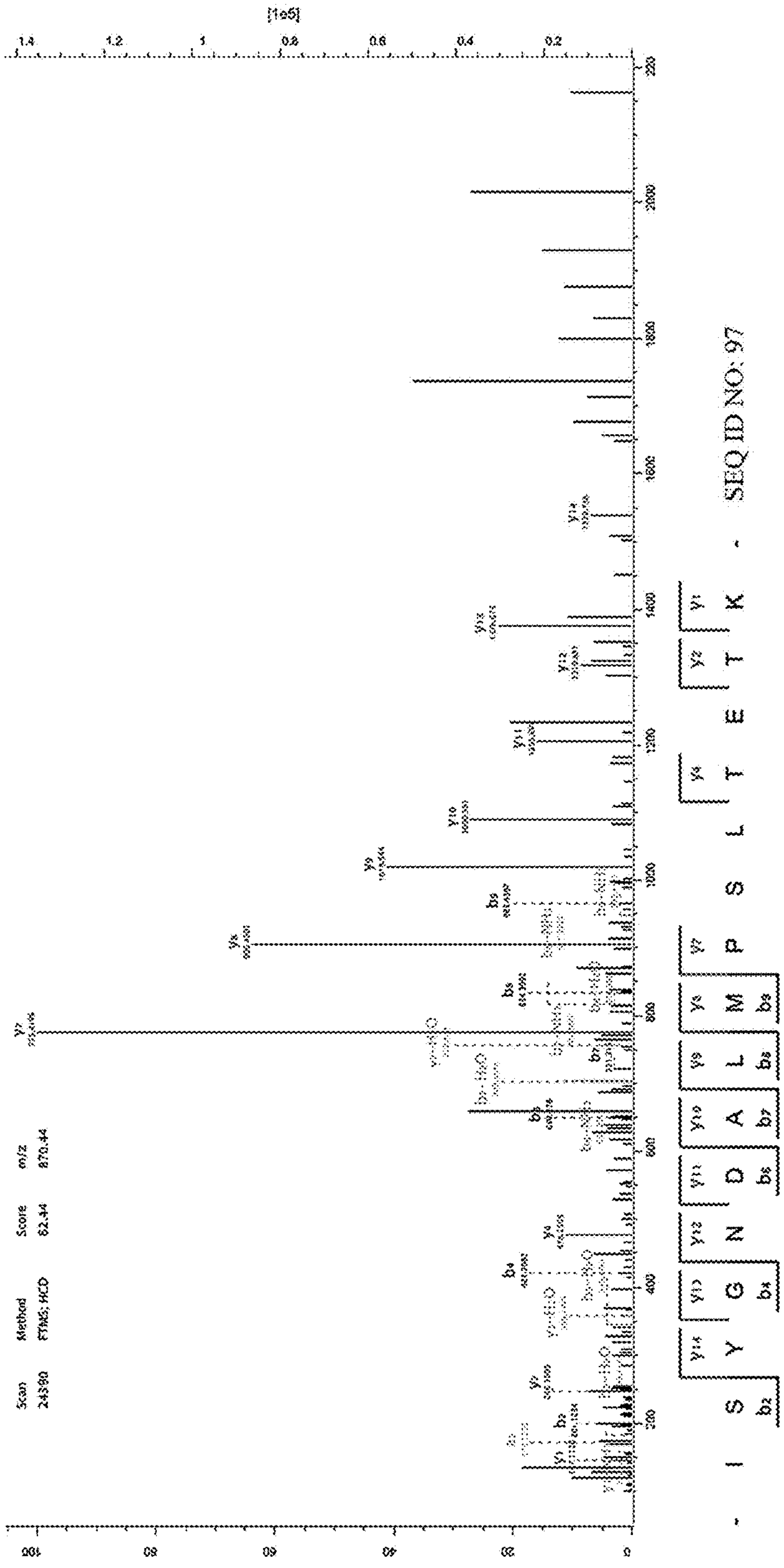
Figure 6D:

FIG. 6A. Antigen positions and detected polypeptides by IP-MS in Aβ175 protein sequence; underlined polypeptides, antigens used for antibody production; black underlined polypeptides, polypeptides detected by Immunoprecipitation-Mass Spectrometry (IP-MS); polypeptide_1, detected The resulting polypeptides are shown in C; polypeptide_2, the detected polypeptides in D. FIG. 6B. Western blot analysis of Aβ175 in human brain samples; control, HEK293 cells were transfected with empty vector; circAβ-a, HEK293 cells were transfected with pCircRNA-DMo-Aβ-a; to prevent complete cleavage of secretase, a was added, β and γ-secretase inhibitors to allow partial cleavage of Aβ175 in HEK293 cells; human brain samples 1-6 were used for this assay; bands 1, 2, 3, 4 are processing of Aβ175 of different lengths from secretase cleavage product. FIG. 6C, FIG. 6D. Mass spectra of polypeptides detected by IP-MS.

Figure 7A:
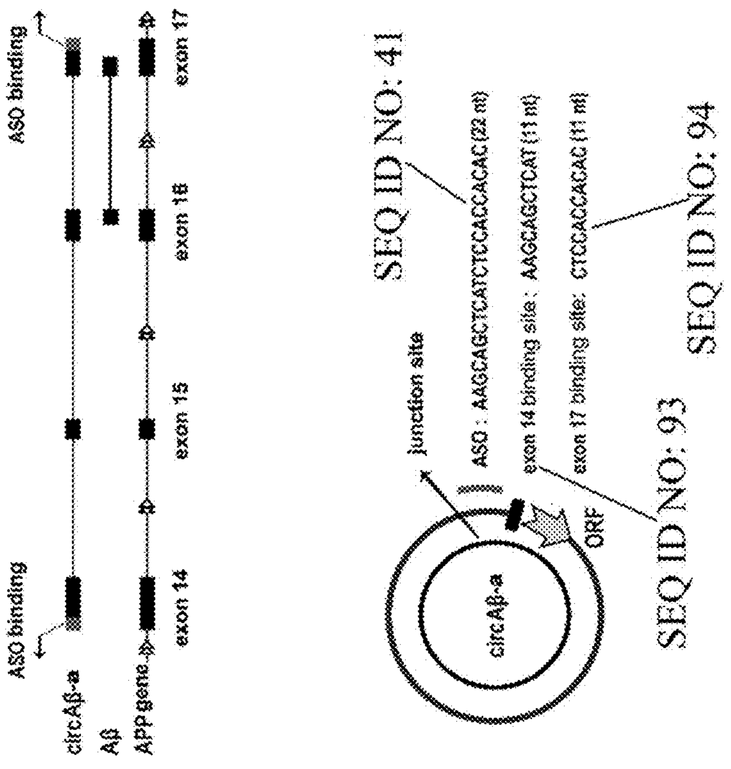
Figure 7B:
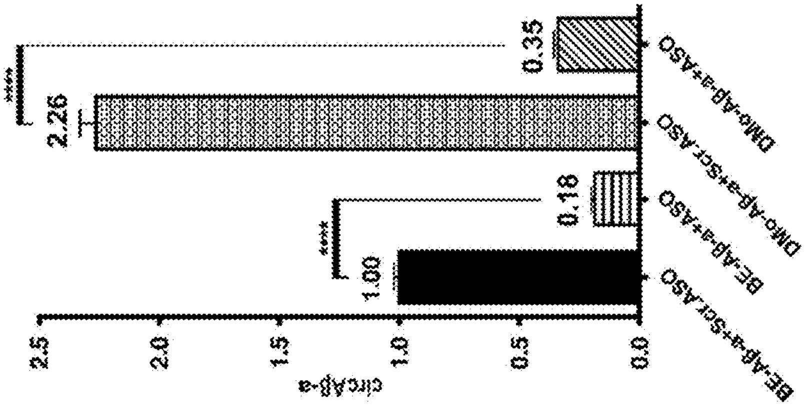
Figure 7C:
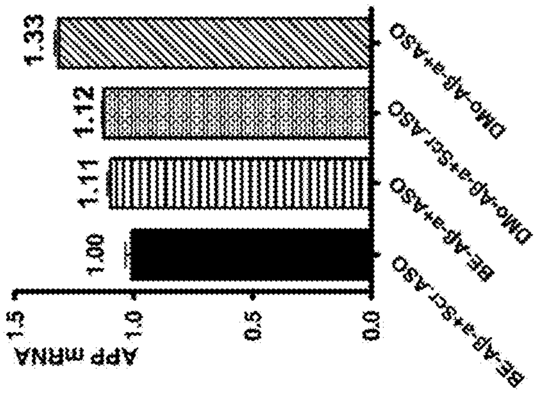

FIGS. 7A-7C. β-amyloid cyclic ribonucleic acid-a (circAβ-a) antisense oligonucleotide (anti-circAβ-a-ASO) reduces the level of circAβ-a in cells. FIG. 7A. Schematic diagram of the designing of anti-circAβ-a-ASO. FIG. 7B. β-amyloid circular ribonucleic acid qRT-PCR results under ASO treatment; BE-AB represents the plasmid overexpressing circAβ-a using pCircRNA-BE vector; DMo-AB represents the overexpression using pCircRNA-DMo vector circAβ-a plasmid; Scr. ASO means negative control experiment ASO. FIG. 7C. qRT-PCR results of APP mRNA under ASO treatment.

Figure 8:
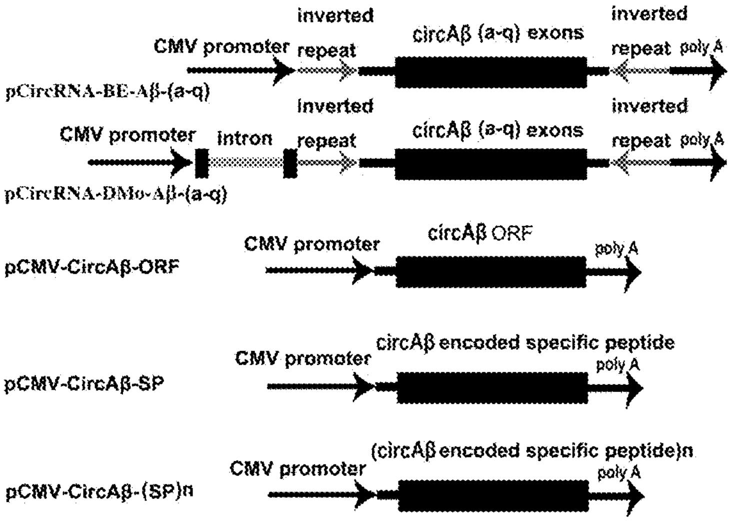

FIG. 8. circAβ and its cDNA expression system.

Figure 9:
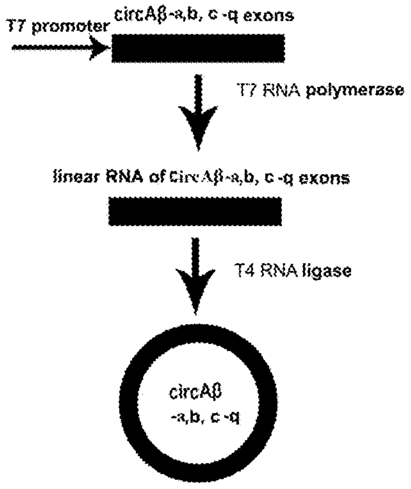

FIG. 9. Schematic diagram of in vitro synthesis of circAβ.

DETAILED DESCRIPTION

Various exemplary embodiments of the present invention will now be described in detail. The detailed description should not be considered as a limitation to the present invention but should be understood as a more detailed description of certain aspects, characteristics, and embodiments of the present invention.

The terms described in the present invention are only used to describe specific embodiments and are not used to limit the present invention. In addition, for the numerical range in the present invention, the upper limit and the lower limit of the range and each intermediate value between them are specifically disclosed. Each smaller range between any stated value or intermediate value within the stated range and any other stated value or intermediate value within the stated range is also included in the present invention. The upper and lower limits of these smaller ranges can be independently included or excluded from the range.

Unless otherwise specified, all technical and scientific terms used herein have the same meaning as commonly understood by those skilled in the art in the field of the present invention. Although the present invention only describes preferred methods and materials, any methods, and materials similar or equivalent to those described herein can also be used in the practice or testing of the present invention. All documents mentioned in this specification are incorporated by reference to disclose and describe methods and/or materials related to the documents. In case of conflict with any incorporated document, the content of this manual shall prevail. Unless otherwise specified, "%" is a percentage based on weight.

In the present invention, the term "circular ribonucleic acid" refers to ribonucleic acid as opposed to linear nucleic acid, which is a ribonucleic acid that has no 3'end and/or 5'end and is connected end to end. The circular ribonucleic acid of the present invention is generally an isolated nucleic acid; or a synthetic nucleic acid, including a chemically synthesized circular ribonucleic acid, and a circular ribonucleic acid obtained by biosynthesis.

In the present invention, the term "polypeptide" refers to multiple amino acids connected to each other by peptide bonds. The amino acids here can be 20 naturally occurring amino acids or modified amino acids. Polypeptides can be modified by any natural method, such as post-translational processing, or by chemical modification techniques known in the art. Modifications can occur anywhere in the polypeptide, including the peptide backbone, amino acid side chains, and the amino or carboxy terminus. It should be noted that in a specific polypeptide, the same type of modification can be performed at multiple sites, or multiple types of modifications can be performed. These modifications include, but are not limited to, acetylation, acylation, ADP-ribosylation, amidation, cross-linking cyclization, disulfide bonding, demethylation, covalent cross-linking, cysteine, pyroglutamate, Formylation, gamma-carboxylation, glycosylation, GPI anchoring, hydroxylation, iodination, methylation, myristoylation, oxidation, proteolysis, and phosphorylation.

In the present invention, the term "specific binding" means that the protein of the present invention preferentially and selectively binds to the target protein relative to other proteins. In certain embodiments, "specific binding" means that the protein of the present invention has greater affinity for the circAβ specific peptide or fragments thereof than other proteins. For example, the equilibrium dissociation constant (KD) value measured by surface plasmon resonance is less than $10^{-7}$ M, preferably less than $10^{-8}$ M, and more preferably less than $10^{-9}$ M.

In the present invention, the term "isolated" refers to a substance such as a nucleic acid, protein, or polypeptide leaving its original environment (for example, if it is naturally occurring, leaving its natural environment). For example, the naturally occurring nucleic acid, protein, or polypeptide in a living animal is not isolated, but the same nucleic acid, protein, or polypeptide isolated from some or all coexisting substances in the natural environment is isolated. It should be noted that such nucleic acid as part of the vector; and/or such nucleic acid, and/or protein or polypeptide as part of the artificially obtained composition are still isolated because these vectors or compositions are not natural. Part is from the environment.

In the present invention, the term "purified" is a relative definition, which does not require complete purification. The "purified" of the present invention includes purification of at least one order of magnitude from artificially obtained mixtures, natural products, or other environments, preferably two or three orders of magnitude, and more preferably four or five orders of magnitude.

In the present invention, the term "host cell", which can also be referred to as a recombinant host cell, refers to a cell into which a recombinant expression vector has been introduced. The host cell includes not only the specific test cell, but also the progeny of this cell. Because certain modifications may occur in subsequent generations due to mutations or environmental influences, such offspring may be different from the parent cell but are still included in the scope of the term "host cell" used in the present invention. The host cells of the present invention include, for example, transfectomas such as CHO cells, NS/0 cells, and lymphocytes.

In the present invention, the term "subject" includes human or non-human animals. "Non-human animals" include all vertebrates, such as mammals and non-mammals, such as non-human primates, sheep, dogs, cows, chickens, amphibians, reptiles, rats, mice, pigs, and the like.

In the present invention, the term "biological sample" refers to a tissue or component derived from a subject. Preferably, the biological sample is derived from a subject suffering from a related disease. Biological samples include body fluids, tissue fluids, or cells or cell populations isolated from a subject. Examples of body fluids include, but are not limited to, blood, serum, plasma, saliva, urine, ascites, cyst fluid, and the like. Examples of tissue fluids include homogenized tissue samples, such as tissue samples obtained by biopsy. The type of cells or cell populations isolated from the subject is not particularly limited, but somatic cells or somatic cell populations are preferred. The biological sample of the present invention may be a mixture of one or more of the above examples. Preferably, the biological sample of the present invention is derived from brain tissue, such as cerebrospinal fluid.

In the present invention, the term "substantially homologous" means that the degree of identity with the target sequence (including base sequence or amino acid sequence) is 50% or more, such as 60% or more, 80% or more or 90% or more, preferably 95% or more; more preferably 97% or more, still more preferably 99%.

In the present invention, the term "stringent conditions" or "stringent hybridization conditions" includes conditions related to the conditions under which the probe will hybridize to its target sequence so that the detectability is greater than other sequences (for example, at least 2 times relative to the background). Stringent conditions are sequence-dependent and vary from environment to environment. By controlling the stringency of hybridization and/or washing conditions, target sequences that can be 100% complementary to primers or probes can be identified (homologous detection). Optionally, stringent conditions can be adjusted to allow certain mismatches in the sequence to detect a lower degree of similarity (heterologous detection).

The stringent conditions of the present invention are wherein the pH is 7.0 to 8.3 and the temperature is at least about 30 (short probes, such as 10 to 50 nucleotides) and at least about 60° C. (long probes, such as greater than 50 nucleotides) The lower salt concentration is less than about 1.5M Na ion, typically about 0.01 to 1.0M Na ion concentration (or other salt). Stringent conditions can also be achieved by adding destabilizing agents such as formamide or Denhardt's solution. Exemplary low stringency conditions include hybridization with a buffer solution of 30 to 35% formamide, 1 M NaCl, 1% SDS (sodium dodecyl sulfate) at 37° C. and 1×to 2×at 50 to 55° C. Wash in SSC (20×SSC=3.0 M NaCl/0.3 M trisodium citrate). Exemplary mild stringent conditions include hybridization in 40 to 45% formamide, 1 M NaCl, 1% SDS at 37° C. and washing in 0.5×to 1×SSC at 55 to 60° C. Exemplary high stringency conditions include hybridization in 50% formamide, 1 M NaCl, 1% SDS at 37° C. and washing in 0.1×SSC at 60 to 65° C.

For washing after hybridization, the key factors are the ionic strength and temperature of the final washing solution. For DNA-DNA hybridization, Tm can be estimated by the following formula: Tm=81.5° C.+16.6 (log M)+0.41 (%

GC)-0.61 (% form)-500/L; where M is the molar concentration of monovalent cations, % GC is the percentage of guanine and cytosine nucleotides in the DNA; % form is the percentage of formamide in the hybridization solution, and L is the length of the hybrid in the base pair. Tm is (under a defined ionic strength and pH) the temperature at which 50% of the complementary target sequence hybridizes to a preferably matched probe. The Tm is reduced by about 1° C. for every 1% of mismatches; therefore, the Tm, hybridization, and/or washing conditions can be adjusted to hybridize to sequences of desired identity. For example, if a sequence with >90% identity is found, Tm can be lowered by 10° C. Generally, stringent conditions are selected to be about 5° C. lower than the thermal melting point (Tm) of the different sequence and its complement at a certain ionic strength and pH. However, very stringent conditions can be used for hybridization and/or washing at 1, 2, 3, or 4° C. lower than the thermal melting point (Tm); mild stringent conditions can be used at 6, 7, 8, 9 lower than the thermal melting point (Tm). Or 10° C. for hybridization and/or washing; low stringency conditions can be used for hybridization and/or washing at 11, 12, 13, 14, 15 or 20° C. lower than the thermal melting point (Tm). Using this equation, the hybridization and wash composition, and the desired Tm, one of ordinary skill will understand that changes in the stringency of hybridization and/or wash solutions are inherently described. If the desired degree of mismatch produces a Tm below 45° C. (aqueous solution) or 32° C. (formamide solution), it is preferable to increase the SSC concentration so that a higher temperature can be used. Unless otherwise specified, in this application, high stringency is defined as 4×SSC, 5×Denhardt's (5 g polysucrose, 5 g polyvinylpyrrolidone, 5 g bovine serum albumin), 0.1 mg/ml at 65° C. Boiled salmon sperm DNA was hybridized with 25 mM sodium phosphate and washed in 0.1×SSC, 0.1% SDS at 65° C.

[β-amyloid Cyclic Ribonucleic Acid]

The first aspect of the present invention provides an isolated or synthesized β-amyloid cyclic ribonucleic acid, which is also referred to herein as "circular ribonucleic acid of the present invention" or "circAβ" for short. The purified circular ribonucleic acid is preferably obtained by isolation or synthesis. The circular ribonucleic acid of the present invention includes the base sequence of at least one exon of the transmembrane amyloid precursor protein (APP) gene or a partial sequence thereof, or a sequence substantially homologous to these sequences and derived from the same species. The circular ribonucleic acid of the present invention may include the entire base sequence of one exon of the 18 exons, or a fragment of one exon, that is, a partial base sequence, or may be substantially homologous to these sequences and derived from Sequence of the same species. The circular ribonucleic acid of the present invention may also include all base sequences of two or more exons among 18 exons, or fragments of partial exons, that is, partial base sequences of partial exons. Preferably, the circular ribonucleic acid of the present invention can express or produce Aβ40 or Aβ42, or fragments thereof, or the circular ribonucleic acid of the present invention includes a base sequence encoding Aβ40 or Aβ42 or fragments thereof.

In certain embodiments, the circular ribonucleic acid of the present invention comprises exon 14, exon 15, exon 16, and exon 17 in the transmembrane amyloid precursor protein (APP) gene. The base sequence of at least one of the exons or a partial sequence thereof, or a sequence substantially homologous to these sequences and derived from the same species. The "partial sequence" here means that it contains at least a base sequence encoding Aβ40 or Aβ42.

In certain embodiments, the circular ribonucleic acid of the present invention comprises base sequences encoding exon 14, exon 15, exon 16, and exon 17, or a partial sequence thereof, or is substantially the same as these sequences. Source and derived from the sequence of the same species. Preferably, the circular ribonucleic acid of the present invention is circAβ-a, and its sequence is shown in SEQ ID NO: 1.

In certain embodiments, the circular ribonucleic acid of the present invention comprises base sequences encoding exon 15, exon 16, and exon 17, or partial sequences thereof, or is substantially homologous to these sequences and derived from the same the sequence of the species. Preferably, the circular ribonucleic acid of the present invention is circAβ-b, the sequence of which is shown in SEQ ID NO: 2.

In certain embodiments, the circular ribonucleic acid of the present invention includes the base sequence encoding exon 16 and exon 17, or a partial sequence thereof, or a sequence substantially homologous to these sequences and derived from the same species. Preferably, the circular ribonucleic acid of the present invention is circAβ-c, and its sequence is shown in SEQ ID NO: 3.

In some embodiments, the circular ribonucleic acid of the present invention includes a base sequence encoding exon 17 or a partial sequence thereof, or a sequence substantially homologous to these sequences and derived from the same species. Preferably, the circular ribonucleic acid of the present invention is circAβ-d, the sequence of which is shown in SEQ ID NO: 4.

In certain embodiments, the cyclic ribonucleic acid of the present invention is circAβ-e, circAβ-f, circAβ-g, circAβ-h, circAβ-i, circAβ-j, circAβ-k, circAβ-I, circAβ-m, CircAβ-n, circAβ-o, circAβ-p or circAβ-q, which are the base sequences or partial sequences encoding different exons or combinations of different exons, respectively.

TABLE 1

Information of exemplary Circular Ribonucleic Acids

| SEQ ID No | Name | circAβ genomic localization | reads number of sample 1 | reads number of sample 2 | reads number of sample 3 | reads number of sample 4 | size (nt) |
|---|---|---|---|---|---|---|---|
| 5 | circAβ-e | chr21:25881397-25891834 | 498 | 445 | 218 | 84 | 488 |
| 6 | circAβ-f | chr21:25881459 -25891868 | 0 | 3 | 25 | 11 | 460 |
| 7 | circAβ-g | chr21:25881489 -25897673 | 21 | 3 | 37 | 1 | 531 |
| 8 | circAβ-h | chr21:25881523 -25897626 | 69 | 108 | 39 | 25 | 450 |
| 9 | circAβ-i | chr21:25881523 -25911815 | 12 | 13 | 0 | 0 | 626 |
| 10 | circAβ-j | chr21:25881537- 25891834 | 0 | 6 | 10 | 4 | 348 |
| 11 | circAβ-k | chr21:25881611 -25891834 | 17 | 20 | 27 | 19 | 274 |

TABLE 1-continued

Information of exemplary Circular Ribonucleic Acids

| SEQ ID No | Name | circAβ genomic localization | reads number of sample 1 | reads number of sample 2 | reads number of sample 3 | reads number of sample 4 | size (nt) |
|---|---|---|---|---|---|---|---|
| 12 | circAβ-l | chr21:25881611 -25891868 | 59 | 37 | 53 | 15 | 308 |
| 13 | circAβ-m | chr21:25881695 -25891855 | 0 | 0 | 20 | 8 | 211 |
| 14 | circAβ-n | chr21:25881695 -25897673 | 35 | 22 | 13 | 17 | 325 |
| 4 | circAβ-d | chr21:25891722 -25891868 | 1519 | 643 | 755 | 571 | 147 |
| 3 | circAβ-c | chr21:25891722 -25897673 | 114 | 100 | 339 | 159 | 248 |
| 2 | circAβ-b | chr21:25891722 -25905077 | 104 | 88 | 218 | 139 | 302 |
| 1 | circAβ-a | chr21:25891722 -25911962 | 1464 | 1113 | 6965 | 3503 | 524 |
| 15 | circAβ-o | chr21:25891733 -25897650 | 0 | 11 | 0 | 25 | 214 |
| 16 | circAβ-p | chr21:25891753 -25891834 | 0 | 51 | 0 | 23 | 82 |
| 17 | circAβ-q | chr21:25891753 -25897626 | 347 | 33 | 73 | 4 | 170 |

In some embodiments, the circular ribonucleic acid of the present invention comprises at least one selected from the sequence shown in SEQ ID NOs: 1-17; or a sequence that is substantially homologous to these sequences and is derived from the same species. Although SEQ ID NOs: 1-17 shows the sequence of ribonucleic acid in a linear sequence, it should be noted that the circular ribonucleic acid of the present invention exists in a circular form. SEQ ID NOs: 1-17 is only for the purpose of illustrating the composition of the sequence.

The circular ribonucleic acid of the present invention can be prepared by a known method. In an exemplary preparation method, it includes synthesizing a circAβ exon DNA fragment containing T7 RNA polymerase by, for example, PCR or plasmid, and then transcribing it into linear circAβ exon RNA by T7 RNA polymerase; and then by T4 RNA ligase Connect linear RNA into circular circAβ RNA. Examples of circAβ include but are not limited to circAβ-a, circAβ-b, circAβ-c, circAβ-d, circAβ-e, circAβ-f, circAβ-g, circAβ-h, circAβ-i, circAβ-j, circAβ-k, CircAβ-1, circAβ-m, circAβ-n, circAβ-o, circAβ-p or circAβ-q.

[Plasmids]

The second aspect of the present invention provides a vector capable of expressing circAβ or producing its cDNA.

In certain embodiments, the vectors of the present invention include circular RNA expression plasmids, examples of which include, but are not limited to, pCircRNA-BE-Aβ, pCircRNA-DMo-Aβ, pCMV-circAβ-ORF, pCMV-circAβ-SP, and pCMV-circAβ-(SP)n. Information about these plasmids is shown in Table 2 below.

TABLE 2

Information about circular RNA expression plasmids or cDNA expression plasmids

| number | constructs | expression product | note |
|---|---|---|---|
| 1 | pCircRNA-BE-Aβ | circAβ | circAβ includes circAβ-a-q shown in Table 1 |
| 2 | pCircRNA-DMo-Aβ | circAβ | circAβ includes circAβ-a-q shown in Table 1 |
| 3 | pCMV-circAβ-ORF | ORF cDNA | |
| 4 | pCMV-circAβ-SP | specific peptide of circAβ translation | SP is a specific peptide, which includes SEQ ID No. 18-23 |
| 5 | pCMV-circAβ-(SP)n | the repeats of specific peptide of circAβ translation | n represents n repetitions, which is a natural number greater than 1 |

[Cells]

The third aspect of the present invention provides a cell in which circAβ, or its cDNA is overexpressed in the cell. Preferably, the cell is an Alzheimer's disease cell model. The cells of the present invention can be prepared by methods known in the art. In an exemplary preparation method, it includes the step of introducing a vector capable of promoting the expression of circAβ or expressing its cDNA into a host cell. In the cell of the present invention, circAβ can be expressed transiently or stably.

[Isolated or Synthetic circAβ Specific Peptide]

The fourth aspect of the present invention provides isolated or synthetic circAβ specific peptides (sometimes referred to as "unique polypeptides" or "unique peptides" in the present invention), which are produced by the cyclic ribonucleic acid of the present invention and are produced in natural A polypeptide does not present in APP protein (or wild type). That is, the circAβ specific peptide cannot correspond to any continuous amino acid sequence fragment of APP.

In some embodiments, the circAβ specific peptide of the present invention comprises a sequence selected from SEQ ID NOs: 18-23, or a sequence that is substantially homologous to these sequences and derived from the same species.

TABLE 3 circAβ specific peptides

| SEQ ID NO. | peptide sequence |
|---|---|
| 18 | MSCFRKSKTIQMTSWPT |
| 19 | LSLLMPALLPTED |
| 20 | GVVEVLG |
| 21 | MIYSLSPFDSCAVTQ |
| 22 | WVDKYQDGGDL |

TABLE 3-continued

| circAβ specific peptides | |
|---|---|
| SEQ ID NO. | peptide sequence |
| 23 | WMQNSDMTQDMKFIIKNWCSLQKMWVQTKVQSLDSWWAVLS |

Note:
The "GVVE" in SEQ ID NO: 20 is derived from APP, and it is combined with the real specific sequence "VLG" into this sequence only for the purpose of showing specificity.

[Isolated or Synthetic Aβ Related Peptides]

The fifth aspect of the present invention provides an isolated or synthesized Aβ-related peptide, which is a polypeptide produced or encoded by the cyclic ribonucleic acid of the present invention. The Aβ-related peptide of the present invention preferably includes a basic sequence and a specific sequence.

The basic sequence of the present invention refers to a sequence composed of multiple consecutive amino acids that is the same as APP or a fragment thereof. Wherein APP refers to a protein composed of 18 exons, and its fragment refers to any one or part of the 18 exons. In the Aβ-related peptide of the present invention, the number of basic sequences is not limited, and it may be one or more.

In some embodiments, the basic sequence of the present invention is an exon derived from at least one of APP exon 14, exon 15, exon 16, and exon 17, or a fragment thereof. In an exemplary embodiment, the basic sequence of the present invention includes the amino acid sequence of Aβ40 or Aβ42 or a fragment thereof. In another exemplary embodiment, the basic sequence of the present invention does not include the amino acid sequence of Aβ40 or Aβ42 or fragments thereof.

The specific sequence of the present invention is the same as the sequence of the circAβ specific peptide, which is a sequence composed of multiple consecutive amino acids produced during translation or expression of the circular ribonucleic acid of the present invention, which is unique in the polypeptide derived from the circular ribonucleic acid The amino acid sequence of, which cannot correspond to the currently known amino acid sequence of APP.

In some embodiments, the specific sequence of the present invention is selected from the sequences shown in SEQ ID NOs: 18-23, or sequences that are substantially homologous to these sequences and are derived from the same species.

In some embodiments, the structure of the Aβ-related peptide of the present invention is basic sequence-specific sequence, specific sequence-basic sequence, first basic sequence-specific sequence-second basic sequence or second basic sequence-specific sequence-first A basic sequence. Among them, the first basic sequence and the second basic sequence are two non-contiguous segments corresponding to APP. Here "-" refers to a chemical bond, especially a peptide bond.

In certain embodiments, the Aβ-related peptides of the present invention comprise the Aβ42 sequence, a specific sequence, and a connecting sequence between the two. Examples of linking sequences include, but are not limited to, sequences such as TVIVITLVMLKKKQYTSIHHGVVE (SEQ ID NO: 90).

In some embodiments, the Aβ-related peptides of the present invention comprise sequences selected from SEQ ID NOs: 24-40, or sequences that are substantially homologous to these sequences and are derived from the same species.

TABLE 4

| Aβ-related peptides | | |
|---|---|---|
| name | number | peptide sequence |
| circAβ-a-DP, Aβ175 | SEQ ID NO: 24 | MISEPRISYGNDALMPSLTETKTTVELLPVNGEFSLDDLQPWHSFGADSVPANTENEVEPVDARPAADRGLTTRPGSGLTNIKTEEISEVKM**daefrhdsgyevhhqklvffaedvgsnkgaiiglmvggvvia**TVIVITLVMLKKKQYTSIHHGVVE**MSCFRKSKTIQMTSWPT** |
| circAβ-b-DP, Aβ80 | SEQ ID NO: 25 | M**daefrhdsgyevhhqklvffaedvgsnkgaiiglmvggvvia**TVIVITLVMLKKKQYTSIHHGVVE**LSLLMPALLPTED** |
| circAβ-c-DP, Aβ70 | SEQ ID NO: 26 | M**daefrhdsgyevhhqklvffaedvgsnkgaiiglmvggvvia**TVIVITLVMLKKKQYTSIHHGVVE**VLG** |
| circAβ-d-DP, 49 | SEQ ID NO: 27 | **mvggvvia**TVIVITLVMLKKKQYTSIHHGVVEVFFAEDVGSNKGAIIGL |
| circAβ-e-DP, 65 | SEQ ID NO: 28 | **mvggvvia**TVIVITLVMLKKKQYTSIHHGVVEVDAAVTPEERHLSKMQQNGYENPTYKEFEQMQN |
| circAβ-f-DP, 102 | SEQ ID NO: 29 | MPELELIHTSVMYSISLYI**lvffaedvgsnkgaiiglmvggvvia**TVIVITLVMLKKKQYTSIHHGVVEVDAAVTPEERHLSKMQQNGYENPTYKFFEQMQN |
| circAβ-g-DP, Aβ100 | SEQ ID NO: 30 | M**daefrhdsgyevhhqklvffaedvgsnkgaiiglmvggvvia**TVIVITLVMLKKKQYTSIHHGVVEVDAAVTPEERHLSKMQQNGYENPTYKFFEQMQN |
| circAβ-h-DP, Aβ115 | SEQ ID NO: 31 | **MIYSLSPFDSCAVTQ**M**daefrhdsgyevhhqklvffaedvgsnkgaiiglmvggvvia**TVIVITLVMLKKKQYTSIHHGVVEVDAAVTPEERHLSKMQQNGYENPTYKFFEQMQN |
| circAβ-i-DP, A13100 | SEQ ID NO: 32 | M**daefrhdsgyevhhqklvffaedvgsnkgaiiglmvggvvia**TVIVITLVMLKKKQYTSIHHGVVEVDAAVTPEERHLSKMQQNGYENPTYKFFEQMQN |
| circAβ-j-DP, 81 aa | SEQ ID NO: 33 | MIYSLSPFDSC**aiiglmvggvvia**TVIVITLVMLKKKQYTSIHHGVVEVDAAVTPEERHLSKMQQNGYENPTYKFFEQMQN |
| circAβ-k-DP, 129 aa | SEQ ID NO: 34 | MVWWRLTPLSPQRSATCPRCSRTATKIQPTSSLSRCRTRPPPQQPLKLDSKTIASLPI**gaiiglmvggvvia**TVIVITLVMLKKKQYTSIHHGVVEVDAAVTPEERHLSKMQQNGYENPTYKFFEQMQN |

TABLE 4-continued

| Aβ-related peptides | | |
|---|---|---|
| name | number | peptide sequence |
| circAβ-l-DP, 65 aa | SEQ ID NO: 35 | mvggvviaTVIVITLVMLKKKQYTSIHHGVVEVDAAVTPEERHLSKMQQNGYENPTY KFFEQMQN |
| circAβ-m-DP, 103 aa | SEQ ID NO: 36 | **mvggvvia**TVIVITLVMLKKKQYTSIHHGVVEVDAAVTPEERHLSKMQQNGYENPTY KRCGFKQRCNHWTHGGRCCHSDSDRHHLGDAEEETVHIHSSWCGGG |
| circAβ-n-DP, Aβ105, 105 aa | SEQ ID NO: 37 | M**daefrhdsgyevhhqklvffaedvgsnkgaiiglmvggvvia**TVIVITLVMLKKKQYTSIHHGVVE VDAAVTPEERHLSKMQQNGYENPTYKF**WVDKYQDGGDL** |
| circAβ-o-DP, Aβ68, 68 aa | SEQ ID NO: 38 | M**daefrhdsgyevhhqklvffaedvgsnkgaiiglmvggvvia**TVIVITLVMLKKKQYTSIHH**DGGD L** |
| circAβ-p-DP, 61 aa | SEQ ID NO: 39 | mvggvviaTVIVITLV1VILKKKQ**CNHWTHGGRCCHSDSDRHHLGDAEEETVQSLDS WWAVLS** |
| circAβ-q-DP, Aβ98, 98 aa | SEQ ID NO: 40 | M**daefrhdsgyevhhqklvffaedvgsnkgaiiglmvggvvia**TVIVITLVMLKKKQ**WMQNSDMT QDMKFIIKNWCSLQKMWVQTKVQSLDSWWAVLS** |

Note:
The lowercase letters are AP-related peptides, and the underlined ones are unique peptides (sequences not available in APP protein)

[Antisense Oligonucleotide]

The sixth aspect of the present invention provides antisense oligonucleotides. The antisense oligonucleotides of the present invention refer to oligonucleotides that are complementary to the target sequence and can hybridize to the target sequence under stringent conditions.

Examples of the antisense oligonucleotides of the present invention include naturally occurring nucleic acid molecules, and derivatives obtained by replacing the phosphate group or the hydroxyl group in the ribose moiety with another more stable group. Specific examples of such antisense oligonucleotide derivatives include the substitution of sulfur for the phosphate group, methyl phosphate group, etc., for the phosphate group, or the hydroxyl group of the ribose moiety being replaced by an alkoxy group such as a methoxy group, an allyloxy group, etc. or Alternative derivatives such as amino groups and fluorine atoms. Preferably methylation modification, phosphorothioate modification (phosphorothioate, PS), morpholino modification (morpholino), peptide nucleic acid (peptide nucleic acid), 2'-O-methylation (2'-O-methyl), Chemical modifications such as 2'-O-(2-methoxyethyl) and locked nucleic acid (LNA). The antisense oligonucleotide of the present invention preferably has a sugar (preferably pentose) structure in its structure because this facilitates the penetration of cell membranes, nuclear membranes, and other structures. The antisense oligonucleotide in the present invention may be of DNA type or RNA type, but from the viewpoint of maintaining high stability after administration, DNA is preferable.

The target sequence of the present invention generally refers to a sequence composed of arbitrary consecutive multiple bases in a circular ribonucleic acid. Preferably, the target sequence is a base sequence encoding a circAβ specific peptide. More preferably, the target sequence is a base sequence encoding at least one polypeptide in the sequence shown in SEQ ID NOs: 18-23.

In certain embodiments, the antisense oligonucleotide of the present invention comprises a sequence selected from SEQ ID NOs: 41-57 or comprises a sequence substantially homologous to these sequences.

TABLE 5

| Exemplary Antisense Oligonucleotides | | |
|---|---|---|
| SEQ ID NO | name | sequence |
| 41 | anti-circAβ-a-ASO | AAGCAGCTCATCTCCACCACAC |
| 42 | anti-circAβ-b-ASO | AACAGGCTCAACTCCACCACAC |
| 43 | anti-circAβ-c-ASO | CAACCCAGAACCTCCACCACAC |
| 44 | anti-circAβ-d-ASO | GCAAAGAACACCTCCACCACA |
| 45 | anti-circAβ-e-ASO | CCAATGATTGCACTAGTTTGATACAG |
| 46 | anti-circAβ-f-ASO | TGCAAAGAACACCAAAATGTAAAG |
| 47 | anti-circAβ-g-ASO | CAACCCAGAACTGATGTGTGGA |
| 48 | anti-circAβ-h-ASO | TCTGCATCCATTTGTGTTACAG |
| 49 | anti-circAβ-i-ASO | CAGGCTGAACTTTGTGTTACAG |
| 50 | anti-circAβ-j-ASO | CAATGATTGCACAGCTGTCAAAAG |
| 51 | anti-circAβ-k-ASO | CAATGATTGCACCGATGGGTAGTG |
| 52 | anti-circAβ-l-ASO | GCAAAGAACACCGATGGGTAGT |
| 53 | anti-circAβ-m-ASO | ACCCACATCTTTTGTAGGTTGG |
| 54 | anti-circAβ-n-ASO | CAACCCAGAACTTGTAGGTTGG |
| 55 | anti-circAβ-o-ASO | ATCTCCTCCGTCATGATGAATG |
| 56 | anti-circAβ-p-ASO | CAATGATTGCACTGTTTCTTCTTC |
| 57 | anti-circAβ-q-ASO | TTCTGCATCCATTGTTTCTTCTTC |

[Inhibitory Ribonucleic Acid Targeting Circular Ribonucleic Acid]

The seventh aspect of the present invention provides an inhibitory ribonucleic acid targeting the circular ribonucleic acid of the present invention or a partial sequence thereof. Examples of the inhibitory ribonucleic acid of the present invention include siRNA, miRNA, or sgRNA targeting circular ribonucleic acid (applied to the CRISPR/Cas gene editing system). Preferably, the inhibitory ribonucleic acid of the present invention comprises the antisense oligonucleotide of the present invention. More preferably, the inhibitory ribonucleic acid of the present invention comprises a sequence selected from SEQ ID NOs: 41-57, or a sequence substantially homologous to these sequences.

[circAβ Specific Peptide Binding Protein]

The eighth aspect of the present invention provides a circAβ specific peptide binding protein, which can specifically bind to the circAβ specific peptide or a fragment thereof of the present invention.

In some embodiments, the circAβ-specific peptide binding protein of the present invention is a circAβ-specific peptide antibody or a modification or a conjugate thereof, which uses circAβ-specific peptide or a fragment thereof as an epitope. The antibodies of the present invention include polyclonal antibodies, monoclonal antibodies, chimeric antibodies, nanobodies, humanized antibodies or fully human antibodies. The antibody of the present invention may be a single chain antibody. The present invention can also provide hybridomas that produce the monoclonal antibodies of the present invention.

In the present invention, modifications of antibodies include chemical modifications and conjugates of antibodies and other materials. Among them, examples of chemical modifications include, but are not limited to, acetylation, acylation, ADP-ribosylation, amidation, cross-linking and cyclization, disulfide bonding, demethylation, covalent cross-linking, cysteine Aminolation, pyroglutamate, formylation, γ-carboxylation, glycosylation, GPI anchoring, hydroxylation, iodination, methylation, myristoylation, oxidation, proteolysis, phosphorylation, etc. Among them, examples of conjugates include, but are not limited to, conjugates with nano-polymer materials, magnetic beads, and the like.

In certain embodiments, the circAβ-specific peptide binding protein of the present invention is an antibody derivative, examples of which include, but are not limited to, a scaffold structure containing one or more complementarity determining regions (CDRs) of the antibody, and one or more variable the scaffold structure of domain (heavy chain or light chain), antibody fragments and variants with specific binding ability of circAβ specific peptide.

The antibody of the present invention can be prepared by a known method. In an exemplary embodiment, the antibody preparation method includes the step of immunizing an animal with an immune antigen, wherein the immune antigen is a circAβ specific peptide or a derivative thereof. Examples of circAβ-specific peptide derivatives include but are not limited to circAβ-specific peptides or conjugates of Aβ-related peptides and carrier proteins. Examples, but not limited to, the carrier protein of the present invention are serum albumin (BSA), chicken ovalbumin (OVA) and keyhole limpet hemocyanin (KLH). In some embodiments, the immune antigen of the present invention has a sequence selected from Table 6.

TABLE 6

| immune antigens | |
|---|---|
| Entry NO | Sequence |
| 1 | **CFRKSKTICIMTSWPT** (SEQ ID NO: 61)-KLH |
| 2 | **LSLLMPALLPTED** (SEQ ID NO: 19)-KLH |

TABLE 6-continued

| immune antigens | |
|---|---|
| Entry NO | Sequence |
| 3 | GVVE**VLG** (SEQ ID NO: 20)-KLH |
| 4 | **MIYSLSPFDSCAVTQ** (SEQ ID NO: 21)-KLH |
| 5 | **WVDKYCIDGGDL** (SEQ ID NO: 22)-KLH |
| 6 | **WMCINSDMTCIDMKFIIKNWCSLCIKMWVCITKVCISLD-SWW AVLS** (SEQ ID NO: 23)-KLH |

The antibodies of the present invention can be produced by known methods. In an exemplary embodiment, the antibody of the present invention is a polyclonal antibody, and its preparation method includes immunizing an animal (for example, New Zealand white rabbit, mouse, or rat with at least one sequence selected from Table 6as an immune antigen) to obtain polyclonal antibodies.

In another exemplary embodiment, the antibody of the present invention is a polyclonal antibody, and its preparation method includes coupling a circAβ specific peptide with keyhole limpet hemocyanin (KLH) to prepare KLH-circAβ-DP-SP as an immune antigen, Use the purified antigen to immunize animals (for example, New Zealand white rabbits, mice or rats, alpaca), collect blood serum, and separate and purify anti-circAβ-DP-SP polyclonal antibodies.

[Pharmaceutical Composition for Preventing or Treating Alzheimer's Disease]

The ninth aspect of the present invention provides a pharmaceutical composition for preventing or treating Alzheimer's disease. The pharmaceutical composition of the present invention comprises the cyclic ribonucleic acid inhibitor and/or circAβ specific peptide inhibitor and/or Aβ related peptide inhibitor of the present invention. Optionally, it further comprises a pharmaceutically acceptable carrier.

The cyclic ribonucleic acid inhibitor of the present invention includes substances capable of reducing, reducing, or blocking the production of cyclic ribonucleic acid of the present invention; substances that reduce, reducing or blocking the expression and translation of corresponding polypeptides by the cyclic ribonucleic acid; and degradation The substance of the circular ribonucleic acid of the present invention. Cyclic ribonucleic acid inhibitors not only include macromolecular compounds, such as polypeptides; they also include small molecular compounds.

In certain embodiments, the circular ribonucleic acid inhibitor of the present invention comprises the antisense oligonucleotide of the present invention. Preferably, the cyclic ribonucleic acid inhibitor of the present invention comprises an oligonucleotide having a sequence selected from SEQ ID NOs: 41-57, or a sequence substantially homologous to these sequences. In certain embodiments, the circular ribonucleic acid inhibitor of the present invention comprises the inhibitory circular ribonucleic acid of the present invention.

The circAβ-specific peptide inhibitor of the present invention includes substances capable of binding (preferably specifically binding) the circAβ-specific peptide or fragments thereof of the present invention; substances that reduce, reduce, or block the production of circAβ-specific peptide from the precursor peptide; reduce, reduce or Substances that block the activity of circAβ-specific peptides; and substances that degrade or decompose circAβ-specific peptides. Such substances can be macromolecular compounds, such as polypeptides; they can also be small molecular compounds.

In some embodiments, the circAβ specific peptide inhibitor of the present invention comprises the circAβ specific peptide binding protein of the present invention. Preferably, the circAβ specific peptide inhibitor of the present invention comprises a circAβ specific peptide antibody.

The pharmaceutically acceptable carrier of the present invention is well known in the art, and those of ordinary skill in the art can determine that it meets clinical standards. Pharmaceutically acceptable carriers include diluents and excipients.

The pharmaceutical composition of the present invention may also contain other ingredients to modify, maintain or maintain the properties of the composition, such as pH, osmolality, viscosity, transparency, color, isotonicity, odor, sterility, stability, dispersion or release rate, adsorption, or permeability characteristics. Examples of suitable other ingredients include, but are not limited to, amino acids (such as glycine, glutamic acid, aspartic acid, arginine or lysine); antibacterial agents, antioxidants (such as ascorbic acid, sodium sulfite or sodium bisulfite), Buffer (such as borate buffer, kind of carbonate buffer, Tris-HCl, citrate buffer, phosphate buffer, Other organic acid buffers), swelling agents (such as mannitol or glycine), chelating agents (such as EDTA), complexing agents (such as caffeine, polyvinylpyrrolidone, β-cyclodextrin or hydroxypropyl-β-ring Formula dextrin), fillers, monosaccharides, disaccharides and other carbohydrates (such as glucose, mannose, or dextrin), proteins (such as serum albumin, gelatin or immunoglobulin), coloring agents, flavoring agents or Diluents, emulsifiers, hydrophilic polymers (such as polyvinylpyrrolidone), low molecular weight peptides, salt-forming counterions, preservatives (such as chloroanisole, benzoic acid, salicylic acid, thimerosal, phenethyl alcohol, Methyl paraben, propyl paraben, chlorhexidine, sorbic acid or hydrogen peroxide), solvent (such as glycerin, propylene glycol or polyethylene glycol), sugar alcohol (such as mannitol or sorbitol), suspending agent, Surfactants or wetting agents, stabilizers (sucrose or sorbitol), tonicity enhancers (such as alkali metal halides), transport carriers, diluents, excipients and/or pharmaceutical adjuvants, etc.

In some embodiments, the pharmaceutical composition of the present invention is a vaccine, which comprises a plasmid capable of expressing the circAβ specific peptide or circAβ related peptide of the present invention, or a fragment thereof. Preferably, the plasmid herein contains a gene capable of producing or expressing the circAβ-specific peptide or circAβ-related peptide of the present invention, or a fragment thereof, and an operating element operably linked to the gene.

Those skilled in the art can determine the optimal pharmaceutical composition according to, for example, the intended route of administration, the form of transportation, and the required dosage. Such a composition can affect the physical state, stability, in vivo release rate, and in vivo clearance rate of the specific binding agent.

The primary vehicle or carrier in the pharmaceutical composition of the present invention can be natural or non-aqueous. For example, a suitable vehicle or carrier can be water, physiological saline, or artificial cerebrospinal fluid for injection, and can be supplemented with other injection administration materials commonly used in the composition. The carrier is, for example, a neutral salt buffer or a serum albumin-salt mixture. Examples of other pharmaceutical compositions include Tirs-buffer (pH about 7.0-8.5) or acetate buffer (pH about 4.0-5.5) and may further include sorbitol or a suitable substitute.

In one embodiment of the present invention, when preparing a pharmaceutical composition for storage, the composition may be mixed with excipients optionally in the form of lyophilized blocks or aqueous solutions. This binding agent product can then be made into a freeze-dried product using a suitable excipient such as sucrose. The pharmaceutical composition can be administered by injection, or via the respiratory tract or intestinal tract, such as oral administration or rectal administration. Those skilled in the art know the preparation method of this pharmaceutically acceptable composition.

When considering administration by injection, the pharmaceutical composition of the present invention may be in the form of a pyrogen-free and injectable aqueous solution, which contains the required inhibitor and a pharmaceutically acceptable carrier containing it. A particularly suitable vehicle for injection is sterile distilled water, in which the inhibitor of the present invention is made into a sterile non-ionic solution and stored properly. Another way that can be used is to combine the required molecules with an agent, such as injectable microspheres, biodegradable particles, polymers (polylactic acid, polyglycolic acid), beads or liposomes, these the reagent allows controlled or sustained release of the desired product, and the preparation is administered by depot injection after preparation.

The pharmaceutical composition suitable for injection administration can also be prepared as an aqueous solution, preferably in a buffer compatible with physiological conditions, such as Hanks's solution, ringer's solution, or physiological saline buffer. An aqueous suspension for injection may contain substances that increase the viscosity of the suspension, such as sodium carboxymethyl cellulose, sorbitol, and dextran. In addition, the active mixture suspension can also be made into a suitable oily suspension. Suitable lipophilic solvents or vehicles include fats such as sesame oil, synthetic fatty acid esters such as ethyl oleic acid, triglycerides, liposomes. The suspension may optionally contain suitable stabilizers or substances capable of increasing the solubility of the compound to allow the preparation of high-concentration solutions.

The present invention can prepare the pharmaceutical composition into a dosage form that can be administered orally. In one embodiment of the invention, the inhibitor administered in this way can be formulated with or without carriers commonly used in solid formulations (for example, tablets or capsules). For example, the capsule can be designed to release the active part of the composition in the gastrointestinal tract when the bioavailability is the greatest and the pre-degradation of the system is the lowest. Other agents can also be used to promote the absorption of the inhibitor. Diluents, flavoring agents, low melting waxes, vegetable oils, lubricants, suspending agents, tablet disintegrating agents, and binders can also be used.

In the present invention, the pharmaceutical composition can also be made into an oral administration form using a pharmaceutically acceptable carrier that is well known in the art and suitable for oral administration dosage forms. These carriers enable the pharmaceutical composition to be formed into a form that can be absorbed by the patient. Such as tablets, pills, dragees, capsules, solutions, gels, syrups, suspensions. Those skilled in the art are also aware of other forms of pharmaceutical compositions, including dosage forms that allow sustained or controlled release of inhibitor molecules. Those skilled in the art are familiar with many other formulation methods for sustained or controlled release delivery, such as liposome carriers, biodegradable microparticles or porous beads.

In the present invention, the pharmaceutical composition for in vivo administration must be sterile. This can be achieved by filtration using a sterile filter membrane. When the composition is in a lyophilized form, this sterilization method can be performed before or after lyophilization (after re-dissolution). The composition for injection can be stored in a lyophilized form or in a solution. In addition, the container for the composition for injection usually has a sterile valve, for example, using an intravenous solution pack or via a stopper that can be pierced by a hypodermic injection needle. Once the pharmaceutical composition has been formulated, it can be packed in a sterile vial in the form of a solution, suspension, gel, emulsion, solid, dehydrated, or lyophilized powder. These preparations can be stored in a ready-to-use form or in a form that needs to be reconstituted before use (such as lyophilization).

In a specific embodiment of the present invention, a kit of packages is used to obtain a single-dose administration unit. The complete package can contain two kinds of containers, the first contains dried protein, and the second contains an aqueous preparation. The present invention also considers the use of this kind of package box, which contains single-cavity or multi-cavity pre-filled syringes (such as liquid syringes and liquid sol syringes).

[Method of Composition for Preventing or Treating Alzheimer's Disease]

The tenth aspect of the present invention provides a method for preventing or treating Alzheimer's disease, which comprises administering to a subject in need thereof a preventive or therapeutically effective amount of a cyclic ribonucleic acid inhibitor and/or circAβ specific peptide inhibitors and/or Aβ-related peptide inhibitors, or the pharmaceutical composition of the present invention.

The preventive or therapeutic effective dose of the present invention depends on, for example, the environment and target of the preventive or therapeutic treatment. Those skilled in the art will understand that the appropriate therapeutic dose level will therefore be different, depending in part on the delivery molecule, the instructions for the use of the binding agent molecule to be used, the route of administration, and the patient's physical (body type, body surface area or organ volume) and conditions (age and general health). Therefore, clinicians can change the dosage and adjust the route of administration to achieve the optimal therapeutic effect. Based on the above factors, a typical dosage may range from about 0.1 mg/kg to 100 mg/kg. In other embodiments, the dosage range is about 0.1 mg/kg-100 mg/kg, or about 1 mg/kg-100 mg/kg, or about 5 mg/kg-100 mg/kg.

It should be noted that the precise dosage should be determined according to the relevant factors of the subject to be treated. The dosage and mode of administration are adjusted to provide a sufficient level of the active compound, or to maintain the desired effect. Factors that are taken into consideration may include the severity of the disease state, the subject's general health, age, weight, gender, timing and frequency of administration, drug compounds, response sensitivity, and treatment response. Depending on the half-life and clearance rate of a particular composition, the frequency of administration of the long-acting pharmaceutical composition can be once every 3 or 4 days, once a week, or once every two weeks.

The frequency of administration of the present invention depends on the pharmacokinetic parameters of the binding agent in the dosage form used. In general, the pharmaceutical composition is administered until the drug achieves the desired effect. Therefore, the composition can be administered in a single dose, or multiple Single administration (at the same or different concentrations/dose), or continuous infusion. Precisely determining the appropriate dose will be routine work. The appropriate dose can be estimated by using appropriate dosing response data.

The administration route of the pharmaceutical composition of the present invention can be in a known manner. Such as oral, intravenous injection, intraperitoneal, intracerebral (intracerebral parenchyma), intracerebroventricular, intramuscular, intraocular, intraarterial, portal vein, intralesional route, intramedullary, intra-cerebrospinal, percutaneous, subcutaneous, intraperitoneal, Intranasal, intestinal, topical, sublingual and through sustained release systems. If necessary, intravenous bolus or continuous infusion can be used.

In some cases, it may be necessary to use the pharmaceutical composition in an in vitro after in vivo manner. In this way, cells, tissues, or organs are removed from the patient, exposed to the pharmaceutical composition, and transplanted back into the patient.

[Method for Diagnosing Alzheimer's Disease]

The eleventh aspect of the present invention provides a method for diagnosing Alzheimer's disease, which includes the step of measuring circAβ and/or circAβ specific peptides in a sample from a subject.

In some embodiments, the diagnostic method of the present invention includes the following steps:

(1) The step of using, for example, a reagent to measure the amount of circAβ and/or circAβ specific peptides in a biological sample from a subject to obtain a measurement value.

(2) The step of comparing the measured value with a standard value, wherein the standard value may be a value obtained from a biological sample of a normal subject equivalent to the age of the subject.

(3) When the measured value is higher than the standard value, the subject is diagnosed as having Alzheimer's disease, or the subject is predicted to be at risk of having Alzheimer's disease.

In some embodiments, the diagnostic method of the present invention includes the following steps:

(a) The step of using, for example, a reagent to measure the content of circAβ and/or circAβ specific peptide in the biological sample collected from the subject at the first time point T1 to obtain the standard value.

(b) Measuring the content of circAβ and/or circAβ specific peptide in the biological sample collected from the same subject at the second time point T2 as the measurement value.

(c) When the measured value is higher than the standard value, the subject is diagnosed as having Alzheimer's disease, or the subject is predicted to be at risk of Alzheimer's disease.

The "reagent" here refers to any reagent that can be used to display the content or level of circAβ and/or circAβ specific peptides, or their fragments. In certain embodiments, the reagents include primers and probes for amplifying circAβ. The primers and probes are described in detail in other positions in this article and will not be repeated here. In some embodiments, the reagent is a circAβ specific peptide binding protein, preferably an antibody. For antibodies, detailed descriptions have been made in other places in this article, so i won't repeat them here.

[Kit for Diagnosing Alzheimer's Disease]

The twelfth aspect of the present invention provides a kit for diagnosing Alzheimer's disease, which contains circAβ and/or circAβ specific peptides, or fragments thereof, which can be used to display, for example, a biological sample from a subject The content or level of any reagent. In some embodiments, the reagents include primers and probes for amplifying circAβ. In some embodiments, the reagent is a circAβ specific peptide binding protein, preferably an antibody.

In certain embodiments, the kit of the present invention includes primers for displaying circAβ in a biological sample from a subject. The primers of the present invention are preferably divergent primer pairs, that is, under stringent conditions, the site where the forward primer hybridizes with the APP gene is located further downstream (i.e., the 3'end) of the site where the reverse primer hybridizes with the APP gene at the divergent direction at 5' end.

The target sequence amplified by the primer pair contains circAβ or a partial sequence thereof. Preferably, the target sequence of the divergent primer of the present invention comprises at least one of exon 14, exon 15, exon 16, and exon 17 of the APP gene or a partial sequence thereof. More preferably, the target sequence of the divergent primer of the present invention comprises exon 17 of the APP gene or a partial sequence thereof. In an exemplary embodiment, the primer sequence of the present invention is shown in SEQ ID NO: 58 (Aβ-VF2) and SEQ ID NO: 59 (Aβ-VR2).

In certain embodiments, the kit of the present invention contains an antibody for displaying circAβ specific peptide in a biological sample from a subject. For antibodies, detailed descriptions have been made in other places in this article, so I won't repeat them here.

The kit of the present invention may also include precautions related to regulating the manufacture, use or sale of the diagnostic kit in a form prescribed by a government agency. The kit can also provide detailed instructions for use, storage, and troubleshooting. The kit may also optionally be provided in a suitable device preferably for robotic operation in a high throughput setting.

The components of the kit of the present invention can be provided as dry powders. When the reagents and/or components are provided as dry powder, the powder can be restored to its original state by adding a suitable solvent. It is expected that the solvent can also be placed in another container. The container will generally include at least one vial, test tube, flask, bottle, syringe, and/or other container means in which the solvent can optionally be placed in aliquots. The kit may also include a second container means for containing sterile, pharmaceutically acceptable buffers and/or other solvents. In the case where there is more than one component in the kit, the kit will usually also contain a second, third or other additional container into which the additional components can be separately placed. In addition, a combination of multiple components may be included in the container.

The kit of the present invention may also include components for holding or maintaining DNA, such as reagents against nucleic acid degradation. Such components may be, for example, RNase-free or nucleases with protection against RNase. Any composition or reagent described herein can be a component of a kit.

[Method for Determining the Effectiveness of Treatment for Alzheimer's Disease]

The thirteenth aspect of the present invention provides a method for determining the effectiveness of treatment for Alzheimer's disease, which includes the step of measuring circAβ and/or circAβ specific peptides, or fragments thereof, in a biological sample from a subject.

In certain embodiments, the method of the present invention for determining the effectiveness of treatment for Alzheimer's disease includes:

(1). The step of using reagents to measure the content of circAβ and/or circAβ specific peptides in biological samples collected from subjects during or after treatment to obtain measured values.

(2). The step of comparing the measured value with the standard value, preferably, measuring the content of circAβ and/or circAβ specific peptide in the biological sample collected from the same subject before the start of treatment as the standard value; and preferably, the standard value is a value obtained from a biological sample of a normal subject equivalent to the age of the subject.

(3). When the measured value is higher than the standard value, it is judged that the treatment is effective, and when the measured value is lower than the standard value, it is judged that the treatment is not effective.

[Method for Screening Useful Compounds for Treating or Alleviating Alzheimer's Disease]

The fourteenth aspect of the present invention provides a method for screening compounds useful for treating or alleviating Alzheimer's disease, which includes the step of measuring circAβ and/or circAβ specific peptides, or fragments thereof, in a sample.

In certain embodiments, the methods of the present invention for screening compounds useful for treating or slowing Alzheimer's disease include:

(1). The step of measuring the content of circAβ and/or circAβ specific peptides in biological samples collected from non-human subjects suffering from Alzheimer's disease to obtain the first measured value.

(2). The step of administering the test compound to the non-human subject.

(3). The step of measuring the content of circAβ and/or circAβ specific peptide in the biological sample collected from the non-human subject after the administration of the test compound to obtain the second measurement value.

(4). The step of comparing the first measurement value and the second measurement value.

(5). When the second measurement value is less than the first measurement value, the test compound is screened as a compound useful for treating or slowing Alzheimer's disease. When the second measurement value is greater than or equal to the first measurement value, the test compound is selected Compound screening is a compound that is not useful for treating or alleviating Alzheimer's disease.

In certain embodiments, the methods of the present invention for screening compounds useful for treating or slowing Alzheimer's disease include:

a. The step of measuring the content of circAβ and/or circAβ specific peptide in cells overexpressing circAβ or its cDNA (preferably the Alzheimer's disease cell model of the present invention) to obtain the first measured value.

b. The step of applying the test compound to the cell.

c. The step of measuring the content of circAβ and/or circAβ specific peptide in the cells after administration of the test compound to obtain the second measurement value.

d. The step of comparing the first measurement value and the second measurement value.

e. When the second measurement value is less than the first measurement value, the test compound is screened as a compound useful for treating or slowing Alzheimer's disease. When the second measurement value is greater than or equal to the first measurement value, the test compound is selected. Compound screening is a compound that is not useful for treating or alleviating Alzheimer's disease.

Example 1

1. Experimental Process:

Identification of circAβ by RT-PCR and Sequencing

The circular RNA containing the Aβ coding region from the APP (amyloid β precursor protein) gene (named circAβ) is obtained by specific "divergent" RT-PCR amplification, that is, a protein that targets the APP gene. The primer encoding exon 17 is divergent orientation, and its sequence is as following:

```
Aβ-VF2
                                   (SEQ ID NO: 58)
atataggatccGTGATCGTCATCACCTTGGTGATGC

Aβ-VR2
                                   (SEQ ID NO: 59)
tatatctcgagCACCATGAGTCCAATGATTGCACC
```

Two total RNAs of human adult normal frontal lobe and hippocampus (R1234051-50-BC, R1234052-10-BC, BioCat GmbH) were used as templates. According to the manufacturer's recommendation, cDNA synthesis was performed with SuperScript™ III First-Strand Synthesis SuperMix (18080400, Invitrogen™) with random hexamer primers. PCR was carried out with PrimeSTAR GXL DNA polymerase (R050A, TaKaRa) and extended 40 cycles at 68° C.

To enrich circular RNA, 15 μl of total RNA from human frontal lobe and hippocampus was treated with 10 units of RNase R (RNR07250, Epicenter) at 37° C. for 1 hour, and purified by phenol-chloroform extraction. The resulting RNA samples were used for subsequent cDNA synthesis and PCR amplification. The PCR product was purified with E.Z.N.A. The gel extraction kit (D2501-02, Omega Bio-tek) was digested with BamHI and XhoI endonuclease (NEB) and ligated into the pCMV-MIR vector (Origene) according to the manufacturer's recommendation. The positive clones were confirmed by Sanger sequencing.

Deep Sequencing

According to the manufacturer's recommendation, use the TruSeq DNA Nano Kit (FC-121-4003, Illumina, Inc) prepare a DNA sequencing library. All libraries were sequenced using HiSeq4000 (Illumina, Inc) system. Approximately one million readings are obtained for each sample, and the STAR aligner (ultra-fast universal RNA-seq aligner) is used for positioning, and then DCC (circRNA computational detection and quantification tool) is used for circRNA detection.

Plasmid Construction and Preparation

Human hsa_circ_000755624,34-36 (circBase) is called circAβ-a in this study. The cDNA of circAβ-a (GRCh37/hg19, chr21: 27264033-27284274) was inserted into the pCircRNA-BE or pCircRNA-DMo vector to produce pCircRNA-BE-Aβ-a or pCircRNA-DMo-Aβ-a. To positively control the expression of Aβ175 protein, the cDNA containing its ORF (open reading frame) was inserted into the pCMV-MIR vector (OriGene). The recombinant plasmid was purified with EndoFree Plasmid Maxi Kit (QIAGEN). All plasmids were verified by restriction endonuclease digestion and Sanger sequencing. Plasmid DNA was purified with EndoFree Plasmid Maxi Kit (QIAGEN).

Cell Culture and Plasmid DNA Transfection

The HEK293 cell line was cultured in Dulbecco's modified Eagle medium (DMEM, Invitrogen™), supplemented with 10% fetal bovine serum (Gibco), 10 mM sodium pyruvate (Sigma), 100 U/ml penicillin and 100 U/ml streptomycin (Gibco) at 37° C., 5% (v/v) $CO_2$. For transient transfection, mix 2.5 μg plasmid DNA diluted in 150 μl Opti-MEM (Invitrogen™) with 5 μl lipofectamine2000 diluted in 150 μl Opti-MEM; add the resulting transfection mixture to a 6-well plate for approximately 50% 10,000 cells. After 24 hours, the transfection mixture was replaced with fresh DMEM medium. Three days after transfection, the cells were harvested for total RNA and protein extraction.

Primary Neuronal Culture and Immunocytochemistry (ICC)

C57BL6N mice were reared according to the guidelines of the European Federation of Laboratory Animal Science Associations (FELASA). Primary neurons were isolated from 13-day-old mouse embryos using a neural tissue dissociation kit according to the manufacturer's recommendations (Miltenyi Biotec). Nucleofection of pCircRNA-DMo-Aβ-a vector or empty vector control (pCircRNA-DMo) was performed with the P3 Primary Cell 4D-Nucleofector™ X kit (V4XP-3024, Lonza Cologne GmbH) according to standard protocols. Transfected neurons were seeded on coated coverslips at a density of $5\times10^6$ cells per well and incubated in MACS neural medium supplemented with 1× MACS NeuroBrew-21 (130-093-566, Miltenyi Biotec) (#130-093-570, Miltenyi Biotec). 1X Glutamine (25030081, Gibco) and 1× Penicillin-Streptomycin (15140122, Gibco). ICC was performed on day 10 after nucleofection with anti-GFP antibody (GFP-1020, Aveslab) and Aβ antibody (6E10, BioLegend Inc.). AlexaFluor® 488 goat anti-chicken IgG (A-11039, thermo scientific) and goat anti-mouse IgG (H+L) cross-adsorbed secondary antibodies (M30010, thermo scientific) were used accordingly as secondary antibodies. Nuclei were stained by DAPI (D9542, Sigma) for 2 hours at room temperature. Images were recorded with a Leica SP8 X confocal microscope.

Total RNA Isolation and qRT-PCR

According to the manufacturer's recommended method, total RNA from HEK293 cells was isolated using TRIzoI reagent (Ambion™). The total RNA of human brain frontal lobe and hippocampus was purchased from BioCat GmbH (R1234051-50-BC, R1234052-10-BC). The total RNA was treated with DNase I (NEB) and purified with phenol and chloroform. For cDNA synthesis using SuperScript® III first-strand synthesis system (Invitrogen™) and random hexamers for priming, 0.5 μg total RNA was used as a template. Power SYBR Green PCR Master Mix (Applied Biosystems™) was used, and 7900HT fast real-time PCR system (Applied Biosystems™) was used for quantitative PCR amplification. The $2^{-\Delta\Delta CT}$ method was used to calculate the fold expression difference between the treated sample and the control sample with β-actin mRNA as an internal control.

TABLE 7

Details of RT-PCR oligonucleotide primers

| circAβ-a primers | | |
|---|---|---|
| circAβ-a-cF | GTCATAGCGACAGTGATCGTC | SEQ ID NO: 62 |
| circAβ-a-cR | CTTGGTTCACTAATCATGTTGGC | SEQ ID NO: 63 |

TABLE 7-continued

| Details of RT-PCR oligonucleotide primers | | |
|---|---|---|
| human APP mRNA primers | | |
| hAPP-mF | TTTGTGATTCCCTACCGCTG | SEQ ID NO: 64 |
| hAPP-mR | TGCCAGTGAAGATGAGTTTCG | SEQ ID NO: 65 |
| human ACTB mRNA primers | | |
| hACTB-F | ACCTTCTACAATGAGCTGCG | SEQ ID NO: 66 |
| hACTB-R | CCTGGATAGCAACGTACATGG | SEQ ID NO: 67 |

Northern Blot Analysis

As mentioned before, NorthernMax™ kit (AM1940, Ambion™) was used for Northern blot hybridization. In short, 15 μg of total RNA from HEK293 cells was separated on a 5% natural polyacrylamide gel (Bio-Rad) and transferred to a positively charged nylon membrane. Hybridization with 5' $P^{32}$-labeled DNA oligonucleotides was performed overnight at 42° C. (Aβ-NBR1: CCCACCATGAGTCCAATGATTGCACCTTTGTTTGAACCCACATCTTCTGCAAAGAACACC, SEQ ID NO: 60).

According to the manufacturer's recommendation, wash the membrane with a kit containing buffer at 42° C. For RNase R treatment, 15 μg of total RNA was digested with 10 units of RNase R (RNR07250, Epicenter) at 37° C. for 1 hour; the resulting RNA was separated by gel electrophoresis and analyzed by Northern blot as described above.

Western Blot Analysis

Prepare protein with RIPA buffer (50 mM Tris-HCl pH 8.0, 150 mM NaCl, 1% (v/v) NP40, 0.1% (w/v) SDS, 0.5% (w/v) Na-deoxycholate, protease inhibitors and phosphatase inhibitors). Separate 40 μg of total protein on 18% or 4-20% Criterion™ TGX Stain-Free™ protein gel (Bio-Rad) and transfer to 0.2 μm nitrocellulose membrane (10600002, Amersham). With anti-β-amyloid (β-amyloid [D54D2] XP® Rabbit mAb, #8243, CST), anti-a-tubulin (#2125, CST) and anti-β-actin (#A5441, Sigma) for western blot analysis. A polyclonal antibody against Aβ175 (anti-Aβ175) was cultured in rabbits, and a unique peptide (SEQ ID NO: 61) was used as the antigen. Human brain samples were purchased from BioCat GmbH and BIOZOL Diagnostica Vertrieb GmbH. Aβ42 (A9810, Sigma) was prepared in DMSO. ImageJ (NIH) was used for quantitative analysis.

Immunoprecipitation-Mass Spectrometry Analysis (IP-MS) of circAβ-a Derived Peptides pCircRNA-DMo-Aβ-a was transfected in HEK293 cells for 24 hours, then 50 nM α-secretase ADAM10 inhibitor GI254023X (SML0789 Sigma), β-secretase inhibitor Begacestat (PZ0187, Sigma) inhibited γ-secretase The agent (SCP0004, Sigma) was added to the cell culture for another 24 hours. The cells were collected and lysed in RIPA buffer. Immunoprecipitation was performed with anti-β-amyloid antibodies 6E10 and 4G8 (803001, 800701, BioLegend Inc.) bound to Dynabeads™ protein A, G (10002D, 10004D, Invitrogen™). The immunoprecipitated protein was digested on the beads by trypsin (V5280, Omega). Mass spectrometry analysis was performed as previously described. For IP-MS of circAβ-a derived peptides from human brain samples, anti-Aβ175 was used in immunoprecipitation with human brain samples-(prepared in RIPA buffer). The remaining steps are carried out as described above.

Immunoprecipitation/Western Blotting (IP-WB) of Aβ Peptide

Aβ peptide detection was performed by immunoprecipitation of conditioned medium (CM), followed by Western blot analysis. In short, HEK293 transfected with pCircRNA-BE-Aβ-a, pCircRNA-DMo-Aβ-a or empty vector (pCircRNA-DMo) The cells were cultured overnight in serum-free medium. Then the CM was prepared with protease and phosphatase inhibitor (Roche), and the master was pre-cleaned with protein A/G (Dynabeads™ Protein A, 10002D, Dynabeads™ Protein G, 10004D, Invitrogen™). Immunoprecipitation was performed with a mixture of Aβ antibodies (6E10, 4G8, BioLegend Inc.). The precipitated peptides were then separated in SDS loading buffer and analyzed by Western blot with an anti-Aβ-derived antibody (D54D2, CST).

2. Results:

circAβ Isoforms are Expressed by the APP Gene in the Human Brain

To experimentally analyze the production of circular RNAs from the Aβ region of the APP gene, RT-PCR amplification was performed using a pair of specific amplification oligonucleotides (FIGS. 1A-1I); total RNA from human frontal lobe and hippocampus was used as a template. This design ensures that the amplified template represents circular RNA from the Aβ region of the APP locus. The resulting PCR products were resolved by native 5% polyacrylamide gel electrophoresis. Analysis revealed the production of various circular RNAs from the A [beta] region (FIG. 1A). To study this amplified circular RNA in more detail, RNA deep sequencing of the corresponding PCR products was used and revealed 17 different isoforms (Table 1). Among these circular RNAs, Hsa_circ_0007556 (circbase, circular RNA database) was detected, and for convenience, it was called circAβ-a (FIG. 1B, Table 1). Similarly, three other circRNAs that were very closely related to circAβ-a were designated as circAβ-b, circAβ-c, and circAβ-d, respectively (FIG. 2B, Table 1).

Confirmation of circAβ by RNA Deep Sequencing

For independent validation of the sequencing analysis, circular RNA identification was performed using the same total RNA that was pretreated with RNase R (which digests linear RNA and leaves circular RNA unaffected). Taken together, 16 of the 17 circAβs were resistant to RNase R treatment, suggesting that they indeed represent circular RNAs. The second round of sequencing analysis revealed another circAβ (Table 1). Importantly, circAβ-a was identified as the most abundant copy (Table 1); this RNA was 4.8/3.1-fold enriched in RNase R-treated frontal and hippocampal RNA samples. Therefore, circAβ-a was chosen as a model to analyze the potential functions associated with circAβ. To analyze the full-length sequence of circAβ-a, RT-PCR products derived from RNase R-enriched samples were cloned into the pCMV-MIR vector. Analysis of circAβ-a containing recombinant clones by Sanger sequencing identified circRNAs consisting of exons 14, 15, 16 and 17 of the APP gene without any traces of retained intron sequences (data not shown).

Finally, to confirm the expression of circAβ-a in selected human brain regions, RT-PCR analysis of human frontal and hippocampal total RNA samples was performed using oligonucleotide primers designed to specifically detect circAβ-a (see FIG. 1B, D). Indeed, circAβ-a was expressed in both the human frontal lobe and hippocampus (FIG. 1D), suggesting that circAβ-a may play a role in memory and cognition.

IME Promotes Overexpression of circAβ-a in Human Cell Lines

To facilitate the study of circRNA function, a strategy based on intron-mediated enhancement (IME) has recently been employed to achieve robust circRNA expression. IME can promote the expression and translation of circRNAs. This approach was applied to enhance circAβ-a expression (FIG. 1C). Transient transfection of pCircRNA-BE-Aβ-a and pCircRNA-DMo-Aβ-a in HEK293 cells resulted in 2185- and 3268-fold overexpression of circAβ-a compared to endogenous background levels, as revealed in controls (FIG. 1D, 1E). Since pCircRNA-DMo-Aβ-a has an IME intron, its enhanced expression of circAβ-a is stronger than that without (pCircRNA-BE-Aβ-a). In addition, Northern blot hybridization was used to monitor circAβ-a expression in HEK293 cells. As shown in FIG. 1F, circAβ-a migrated much faster than its linear RNA counterpart. At the same time, the signal of circAβ-a is not affected by RNase treatment, so it is indeed circular RNA expressed in HEK293.

Importantly, RNA hybridization revealed that neither pCircRNA-BE-Aβ-a nor pCircRNA-DMo-Aβ-a produced mature linear mRNA variants, thus ruling out the possibility of linear RNA contamination in subsequent functional assays. Finally, RT-PCR analysis and Sanger sequencing revealed transient expression and consistency of circAβ-a in human brain (FIGS. 1G, 1H, 1I).

In conclusion, it can be concluded that circAβ-a is strongly expressed in HEK293 cells through the IME effect. Since HEK293 cells represent a mature cell model for Alzheimer's disease-related research. Therefore, the IME system for circAβ-a expression in HEK293 cells provides a very suitable model for analyzing circAβ-a function.

circAβ-a can be Translated into Aβ-Related Peptides in Human Cell Lines

ORFs of at least some circular RNAs have been shown to be translatable. Detection of circAβ-a identified an open reading frame (ORF) of 19.2 kDa (FIGS. 2A, 2D), therefore, western blotting was performed to investigate whether circAβ-a was translated into Aβ-related polypeptides. Significant Aβ-related polypeptide signals with a size of approximately 15 to 20 kDa were detected by this study, confirming the translation of circAβ-a in the HEK293 system (FIG. 2B). The circAβ-a translation product was called circAβ-a-derived peptide (circAβ-a-DP or Aβ175 because it has 175 amino acids, FIG. 2D). Compared with the endogenous level in HEK293 cells, pCircRNA-DMo-Aβ-a had about 3.3-fold stronger protein expression, whereas plasmid pCircRNA-BE-Aβ-a had only 1.4-fold more Aβ-related polypeptides (FIGS. 2B, 2C).

To further investigate the cyclic translation products derived from circAβ-a, Aβ175 was immunoprecipitated with anti-Aβ antibodies (6E10, 4G8), and the resulting peptides were analyzed by subsequent mass spectrometry. As shown in FIGS. 2A-2D, there is a unique stretch of amino acid sequence in the A [beta] 175 peptide sequence, which is the result of circular translation (FIG. 2D, uppercase underlined); this peptide sequence is completely absent in the full-length APP because it represents the cyclized product. Mass spectral signals corresponding to unique polypeptides were obtained (SKTIOMTSWPT, FIGS. 2D, 2E). Therefore, these results indicate that circAβ-a is indeed translated into Aβ-related polypeptides.

Further Processing of Aβ175 to Form Aβ in Human Cell Lines

The translation of Aβ-related polypeptides from the circAβ-a template underscores the significant potential for circRNA-dependent Aβ polypeptide generation. Notably, the predicted primary structure of Aβ175 contained β- and γ-secretase cleavage sites, suggesting that potential Aβ-related products may be generated from Aβ175 through β- and γ-secretase-mediated cleavage (FIG. 2D). Specific anti-Aβ-antibodies (6E10, 4G8, mouse antibodies) were used for immunoprecipitation and subsequent western blotting (IP-WB) to analyze the presence of Aβ expression in the conditioned medium (CM) of circAβ-a overexpressing HKE293 cells.

Strikingly, a peptide signal corresponding to Aβ was observed in western blot with another Aβ antibody (D54D2, rabbit antibody), confirming the generation of Aβ from translation of circAβ-a (FIGS. 3A, 3B). Compared with HEK293 transfection with empty vector used as a negative control, pCircRNA-BE-Aβ-a caused an approximately 2.6-fold increase in Aβ polypeptide expression in conditioned medium (FIGS. 3A, 3B). Strikingly, pCircRNA-DMo-Aβ-a enhanced Aβ polypeptide expression more than 6-fold (FIGS. 3A, 3B). Notably, the detected differences in Aβ expression for the three samples (control, pCircRNA-BE-Aβ-a, pCircRNA-DMo-Aβ-a) were consistent with changes in Aβ175 levels, suggesting that the upregulated Aβ is derived from Aβ175.

circAβ-a Overexpression Develops into Aβ Plaques in Primary Neuronal Cultures

The present invention also investigated whether these Aβ polypeptides, which are the result of circRNA translation, would develop into Aβ plaques outside neurons. The latter is a hallmark of the development of neuropathology in Alzheimer's disease. For analysis, pCircRNA-DMo-Aβ-a vector was transfected into mouse embryonic neurons and screened with anti-Aβ antibody 6E10 to find Aβ plaques within neuronal cultures after 10 days of incubation. Signals of Aβ plaque formation were specifically observed in neuronal cultures expressing circAβ-a (arrows in FIG. 3D). Neuronal cell cultures transfected with empty vector were used as negative controls, and there was no significant signal of A [beta] plaque formation (FIG. 3C). Both the empty and circAβ-a expression vectors contain a GFP expression cassette, and immunohistochemistry for GFP allows labeling of transfected neuronal cells. The combination of GFP and AB plaque signals indicated that plaques are specifically located outside neurons, which is consistent with our current understanding of Alzheimer's disease pathophysiology (FIG. 3D).

In conclusion, it can be concluded that circAβ-a expression leads to Aβ plaque formation in primary neuronal cell cultures.

3. Discussion

Previous studies have conclusively demonstrated Aβ biogenesis in familial Alzheimer's disease, but Aβ production in sporadic Alzheimer's disease remains unknown. The present invention found 17 different circAβ from APP gene. With the help of intron-mediated circRNA expression and translation enhancement technology, it was found that circAβ-a can be translated into Aβ-related polypeptide (Aβ175). Furthermore, Aβ175 was processed and developed into Aβ plaques, suggesting a potential new avenue and direction to search for the molecular mechanisms of Alzheimer's disease (FIG. 4). This mechanism is significantly different from Aβ induced by proteolytic processing of full-length APP (FIG. 4). Therefore, it provides an alternative pathway for Aβ biogenesis (FIG. 4). Unlike mutations known to be responsible for familial forms of Alzheimer's disease, specific mutations are not required for circAβ biogenesis. This suggests that the entire population may express circAβ, and thus its protein product, circAβ-DP, suggesting that it may play a key role in the pathogenesis of sporadic Alzheimer's disease. The biological role of circAβ may not only reveal new mechanisms that cause Alzheimer's disease but may also pave the way for developing new strategies for the diagnosis, prevention, and treatment of Alzheimer's disease. In addition, the key coding functions of circAβ-a in neurological diseases suggest that circAβ-b and circAβ-c may also generate Aβ precursors through protein coding, thereby playing an important pathogenic role in Alzheimer's disease.

Example 2

This example is the preparation of polyclonal antibodies. The immune antigen is a circAβ-specific peptide (circAβ-DP-SP, FIG. 5, FIG. 6, Table 3). The circAβ-DP specific peptide was coupled with KLH to obtain conjugates, the amino acid sequences of which are shown in SEQ ID NO: 57 and Entry Nos. 1 and 2 of Table 6, respectively. Using any of these conjugates as an immunogen, a polyclonal antibody against circAβ-DP-SP was obtained by immunizing New Zealand white rabbits (or mice and other animals).

The purified antigen was used to immunize New Zealand white rabbits, the rabbit blood serum was collected, and the polyclonal antibodies against circAβ-DP-SP rabbits were isolated and purified. The purity of the antibody serum can reach more than 50% after affinity chromatography. The prepared antibody has undergone indirect enzyme-linked immunosorbent assay and western blot analysis experiments, and the surface has the characteristics of high specificity and high affinity.

Results of indirect enzyme-linked immunosorbent assay:
Coating antigen: free peptide
Coating antigen concentration: 4 μg/ml, 100 μl/well
Coating antigen buffer: phosphate buffered saline, pH 7.4
Secondary antibody: Anti-rabbit IgG Fc monoclonal secondary antibody (HRP conjugate)
Antigen peptide sequence: CFRKSKTIQMTSWPT (SEQ ID NO: 61)
Immunogen: Antigenic peptide-carrier protein (KLH)
Immunized animals: New Zealand white rabbits

TABLE 8

| Antibody Information | | | | | | | | |
|---|---|---|---|---|---|---|---|---|
| | NC | 1 | 2 | 3 | 4 | 5 | black | Titer |
| dilution | 1:1,000 | 1:1,000 | 1:2,000 | 1:4,000 | 1:8,000 | 1:16,000 | | |
| animal #1 | 0.064 | 2.871 | 2.679 | 2.518 | 2.138 | 1.759 | 0.049 | >1:16,000 |
| animal #2 | 0.077 | 2.764 | 2.509 | 2.188 | 1.834 | 1.237 | 0.049 | >1:16,000 |

The titer is the highest dilution when S/B (signal/blank) >=2.1, and the OD450 in the blank is the average of two technical replicates. NC is a negative control (pre-immune serum).

TABLE 9

| Purified antibodies | | | | | |
|---|---|---|---|---|---|
| antibody source | volume (ml) | concentration (mg/ml) | amout (mg) | purity | purification method |
| animal #1 | 7.50 | 0.453 | 3.39 | 50% | Antigen peptide affinity chromatography |
| animal #2 | 7.50 | 0.175 | 1.31 | 55% | Protein A Affinity Chromatography |

Expression of circAβ-a Translation Peptide in Human Brain

The present invention demonstrates that circAβ-a is translated into Aβ-related peptides in cell lines and primary neuron cultures. These data suggest a potential role for these circRNAs in Alzheimer's disease pathology. For in vivo analysis of potential circAβ-a-related functions in Alzheimer's disease, human brain samples were screened for Aβ175 (circAβ-a-DP). For this purpose, antibodies specific for the C-terminal domain of Aβ175 have been generated (anti-Aβ175, FIG. 6A). The C-terminus of Aβ175 contains a unique sequence consisting of 17 amino acids. This domain was able to distinguish Aβ peptides derived from Aβ175 from APP proteins; Western blot hybridization with anti-Aβ175 antibody finally confirmed the expression of AB peptides derived from circAβ-a translation in human brain. Indeed, this study also found several specific signals in the Western blot ranging from 20 to 40 kDa (FIG. 6B). HEK293 cells expressing circAβ-a were used as a positive control and marker for Aβ175 migration in gel electrophoresis (FIG. 6A). Note, to prevent complete cleavage of Aβ175 in HEK293 cells by secretase, a, B and γ-secretase inhibitors were added to allow partial cleavage. Several specific signals were found reflecting secretase-catalyzed proteolytic addition to A [beta] 175 (FIGS. 6A, 6B). Furthermore, to unequivocally demonstrate the identity of these peptides detected in Western blot hybridization, immunoprecipitation/mass spectrometry (IP-MS) analysis of human brain extracts (in RIPA buffer) was performed with this specific antibody (anti-Aβ175). Two peptides located at the N-terminus of Aβ175 (peptide_1 in FIG. 6A, FIG. 6C) and another peptide located in the C-terminal region were detected, covering the unique part of Aβ175 (peptide 2 in FIGS. 6A, FIG. 6D). These results were consistent with the in silico inferred amino acid sequence (FIG. 6A) and Western blot analysis (FIGS. 6A, 6B).

The AD diagnostic method based on blood or cerebrospinal fluid detection established according to the research results will be the world's first efficient, sensitive, stable, and reliable minimally invasive detection method. In the future, testing procedures and costs will be greatly simplified, reducing harm to patients. The clinical application will also more accurately evaluate the treatment effect and screen real healthy and AD patients for drug testing, to establish and improve a comprehensive AD diagnosis system.

Example 3

In this example, the specific antisense oligonucleotide (ASO) against β-amyloid cyclic ribonucleic acid (circAβ) is used to inhibit and degrade circAβ to prevent and treat Alzheimer's disease. As shown in FIGS. 7A-7C, the level of the circular RNA in the cell is reduced by antisense oligonucleotides (anti-circAβ-a-ASO) against β-amyloid cyclic ribonucleic acid-a (circAβ-a). The APP mRNA was not affected (FIG. 7C). As shown in the figure, antisense oligonucleotides containing SEQ ID NOs: 41-57 anti-β amyloid cyclic ribonucleic acid (circAβ). Antisense oligonucleotides recognize β-amyloid circular ribonucleic acid through base complementary pairing. Antisense oligonucleotides that bind target RNA can degrade target RNA by activating RNase H enzyme activity (FIGS. 7A-7C). Antisense oligonucleotides can also regulate (such as inhibit) protein translation by binding to target RNA.

Example 4

This example is the construction of a cell model. The expression system of circAβ and its cDNA was introduced into the cells to establish a stable cell line, thereby obtaining a new cell model of Alzheimer's disease. As shown in FIG. 8, the expression system of circAβ and its cDNA were constructed. Among them, pCircRNA-BE-AB represents a plasmid that expresses circAβ (a, b, c-q) through the circular RNA expression plasmid pCircRNA-BE. pCircRNA-DMo-Aβ refers to a plasmid that expresses circAβ (a, b, c-q) through the circular RNA expression plasmid pCircRNA-DMo. pCMV-circAβ-ORF means a plasmid that overexpresses the ORF cDNA encoding the polypeptide of circAβ. pCMV-circAβ-SP represents a plasmid that overexpresses circAβ specific polypeptide. pCMV-circAβ-(SP) n represents a plasmid that overexpresses circAβ-specific polypeptide multiple times; n represents one, two or more repetitions. circAβ includes but is not limited to circAβ-a, circAβ-b, circAβ-c.

Example 5

This example is a specific biosynthesis method of circAβ, which is described in detail as following:

1. Generation of pCircRNA-BE-Rtn4

To construct the circRtn4 expression plasmid, the genomic region containing the circRtn4 exon (chr11: 29,704,497-29,708,881, mouse GRCm38/mm10) includes part of the 5' and 3'flanking intron sequences (1014 bp and 111 bp). The oligonucleotide primers listed in Table 10 were used to amplify by PCR from a genomic DNA template isolated from mouse N2a cells. The resulting product was inserted into pCMV-MIR (OriGene) containing the CMV promoter for expression. The resulting plasmid is called control-2. The inverted repetition contributes to the efficiency of recovery, and in turn produces circular RNA. For this purpose, a region of 800 nucleotides was selected to represent the 5'intron portion of Control-2 (corresponding to chr11: 29,704,521-29,705,320). This region is incorporated into the 3'flanking intron to create the downstream portion of the inverted repeat. Therefore, its relative orientation in the resulting box is reversed compared to its 5'intron counterpart. Since flanking introns lack 5' and 3'splice sites, they cannot support canonical splicing reactions and produce linear mRNA. The resulting plasmid was named pCircRNA-BE-Rtn4.

2. Generation of pCircRNA-DMo-Rtn4 pCircRNA-DMo-Rtn4 is produced by the pCircRNA-BE-Rtn4 vector, inserted into the chimeric intron from pCI-neo-FLAG, upstream of the circRNA domain. The primers used are shown in Table 10 below.

TABLE 10

| Primer Information | | |
|---|---|---|
| mouse β-Actin mRNA qRT-PCR primers | | |
| ActbF1 | ACCTTCTACAATGAGCTGCG | SEQ ID NO: 66 |
| ActbR1 | CTGGATGGCTACGTACATGG | SEQ ID NO: 68 |
| human β-Actin mRNA qRT-PCR primers | | |
| Human ACTB-F | TCGTGCGTGACATTAAGGAG | SEQ ID NO: 69 |
| Human ACTB-R | TTGCCAATGGTGATGACCTG | SEQ ID NO: 70 |
| pCircRNA-BE-Rtn4 plasmid construction primers | | |
| i-Rtn4-BF | AATTAAGGATCCATGGGAATTCACGTGATTCTCC | SEQ ID NO: 71 |
| i-Rtn4-XR | TTAATTCTCGAGCTACTAGAAAACACAGCTAACAGAATGC | SEQ ID NO: 72 |
| IvRtn4I-BF | AATTAAGGATCCAACGTTAACCCTGTAATGAATACTG | SEQ ID NO: 73 |
| IvRtn4I-XR | ACTTTGCTCGAGCTCATCAACATGACACAGTAGACATG | SEQ ID NO: 74 |
| IvRtn4II-XF | ATGAGCTCGAGCAAAGTGATTTTCCACACAGTATTATCAC | SEQ ID NO: 75 |
| IvRtn4II-XR | TTAATTCCCGGGCAACGTTAACCCTGTAATGAATACTG | SEQ ID NO: 76 |
| pCircRNA-DMo-Rtn4 plasmid construction primers | | |
| pCI-CMV-F | ATGTCCAATATGACCGCCATGTTG | SEQ ID NO: 77 |
| pCI-Intron-R | aacgttgGATCCAGTCGACCTATAGTGAGTCGTATTAAGTACTCTAGCCTTAAGAGC | SEQ ID NO: 78 |

TABLE 10-continued

| Primer Information | | |
|---|---|---|
| pCircRNA-DMo plasmid construction primers | | |
| CicrI-F | CTATAGGTCGACTGGATCcaacgttaacc | SEQ ID NO: 79 |
| CicrI-R | tctagaccgcggccgcgatatcgctagcagatctTCTCATctgaaaaacaaacagaata-caacctcag | SEQ ID NO: 80 |
| CV-MCS-F | agatctgctagcgatatcgcggccgcggtctagaCTTCAGgtaataatccatgcaccgtctc | SEQ ID NO: 81 |
| CV-MCS-R | cactttgCTCGAGctcatcaacatg | SEQ ID NO: 82 |
| overlap PCR primers | | |
| circDMO-LF | GTCGACTGGATCcaacgttaaccc | SEQ ID NO: 83 |
| circDMO-LR | GCTGTCGTGGGAActgaaaaacaaacagaatacaacctcagc | SEQ ID NO: 84 |
| circDMO-RF | TCAAGATGAAGTCGgtaataatccatgcaccgtctcacc | SEQ ID NO: 85 |
| circDMO-RR | cactttgCTCGAGctcatcaacatg | SEQ ID NO: 82 |
| pCircRNA-BE-Aβ-a and pCircRNA-DMo-Aβ-a plasmid construction primers | | |
| Abeta-circF | gtagttatcagATGAGCTGCTTCAGAAAGAGCAAAACT | SEQ ID NO: 86 |
| ABeta-circR | gcatggattattacCTCCACCACACCATGATGAATGG | SEQ ID NO: 87 |
| DMo-Ab-LR | CTGAAGCAGCTCATctgaaaaacaaacagaatacaacctcagc | SEQ ID NO: 88 |
| DMo-Ab-RF | GGTGTGGTGGAGgtaataatccatgcaccgtctcacc | SEQ ID NO: 89 |

3. Production of pCircRNA-BE and pCircRNA-DMo

To construct a general vector for circRNA expression, multiple restriction endonuclease sites (BglII, NheI, BmtI, EcoRV, NotI, SacII, XbaI) were added to the original circRtn4 of pCircRNA-BE-Rtn4 or pCircRNA-DMo-Rtn4, leading to the vector pCircRNA-BE or pCircRNA-DMo. The oligonucleotide primers used are shown in Table 10.

4. Production of pCircRNA-BE-Aβ-a, b, c-q and pCircRNA-DMo-Aβ-a, b, c-q

As shown in FIG. 8, insertion the coding DNA sequence of circAβ-a, circAβ-b, circAβ-c, . . . circAβ-q into the two vectors pCircRNA-BE and pCircRNA-DM to form the expression of circAβ-a, circAβ-b, circAβ-c . . . the plasmid of circAβ-q.

5. In Vitro Synthesis Method of circAβ

As shown in FIG. 9, the circAβ exon DNA fragment containing T7 RNA polymerase is first synthesized by PCR or plasmid, and then transcribed into linear circAβ exon RNA by T7 RNA polymerase; RNA is connected into circular circAβ RNA; circAβ includes but is not limited to circAβ-a, circAβ-b, circAβ-c.

Note:

Without departing from the scope or spirit of the present invention, various improvements and changes can be made to the specific embodiments of the present specification, which is obvious to those skilled in the art. Other embodiments derived from the description of the present invention will be obvious to the skilled person. The specification and examples of this application are only exemplary.

The invention claimed is:

1. An antisense oligonucleotide, comprising an oligonucleotide that is synthetic and chemically-modified, having one or more chemical modifications selected from the group consisting of phosphorothioate, 2'-O-methyl, 2'-O-(2-methoxyethyl), locked nucleic acid (LNA), morpholino, and peptide nucleic acid (PNA), complementary to and capable of hybridizing with a target sequence, wherein the target sequence comprises a sequence of a β-amyloid cyclic ribonucleic acid (circAβ), the circAβ comprising a back-splice junction (BSJ) region and a base sequence of at least one exon of the transmembrane amyloid precursor protein (APP) gene or a partial sequence thereof, or a sequence that is substantially homologous to the sequence and derived from the same species, wherein the circAβ is capable of expressing or producing Aβ40 or Aβ42, or fragments thereof, and comprises at least one sequence selected from the group consisting of SEQ ID NOS: 1-17, and wherein the antisense oligonucleotide comprises a sequence selected from the group consisting of SEQ ID NOS: 41-57 and hybridizes under stringent conditions to circAβ but not detectably to linear APP mRNA.

2. A pharmaceutical composition for treating Alzheimer's disease, comprising a circAβ inhibitor according to claim 1 and a pharmaceutically acceptable carrier.

* * * * *

SEQUENCE LISTING

```
<160> NUMBER OF SEQ ID NOS: 98

<210> SEQ ID NO 1
<211> LENGTH: 524
<212> TYPE: DNA
<213> ORGANISM: Homo sapiens

<400> SEQUENCE: 1

atgagctgct tcagaaagag caaaactatt cagatgacgt cttggccaac atgattagtg     60
```

aaccaaggat cagttacgga aacgatgctc tcatgccatc tttgaccgaa acgaaaacca 120
ccgtggagct ccttcccgtg aatggagagt tcagcctgga cgatctccag ccgtggcatt 180
cttttggggc tgactctgtg ccagccaaca cagaaaacga agttgagcct gttgatgccc 240
gccctgctgc cgaccgagga ctgaccactc gaccaggttc tgggttgaca aatatcaaga 300
cggaggagat ctctgaagtg aagatggatg cagaattccg acatgactca ggatatgaag 360
ttcatcatca aaaattggtg ttctttgcag aagatgtggg ttcaaacaaa ggtgcaatca 420
ttggactcat ggtgggcggt gttgtcatag cgacagtgat cgtcatcacc ttggtgatgc 480
tgaagaagaa acagtacaca tccattcatc atggtgtggt ggag 524

<210> SEQ ID NO 2
<211> LENGTH: 302
<212> TYPE: DNA
<213> ORGANISM: Homo sapiens

<400> SEQUENCE: 2
ttgagcctgt tgatgcccgc cctgctgccg accgaggact gaccactcga ccaggttctg 60
ggttgacaaa tatcaagacg gaggagatct ctgaagtgaa gatggatgca gaattccgac 120
atgactcagg atatgaagtt catcatcaaa aattggtgtt ctttgcagaa gatgtgggtt 180
caaacaaagg tgcaatcatt ggactcatgg tgggcggtgt tgtcatagcg acagtgatcg 240
tcatcacctt ggtgatgctg aagaagaaac agtacacatc cattcatcat ggtgtggtgg 300
ag 302

<210> SEQ ID NO 3
<211> LENGTH: 248
<212> TYPE: DNA
<213> ORGANISM: Homo sapiens

<400> SEQUENCE: 3
gttctgggtt gacaaatatc aagacggagg agatctctga agtgaagatg gatgcagaat 60
tccgacatga ctcaggatat gaagttcatc atcaaaaatt ggtgttcttt gcagaagatg 120
tgggttcaaa caaaggtgca atcattggac tcatggtggg cggtgttgtc atagcgacag 180
tgatcgtcat caccttggtg atgctgaaga agaaacagta cacatccatt catcatggtg 240
tggtggag 248

<210> SEQ ID NO 4
<211> LENGTH: 147
<212> TYPE: DNA
<213> ORGANISM: Homo sapiens

<400> SEQUENCE: 4
gtgttctttg cagaagatgt gggttcaaac aaaggtgcaa tcattggact catggtgggc 60
ggtgttgtca tagcgacagt gatcgtcatc accttggtga tgctgaagaa gaaacagtac 120
acatccattc atcatggtgt ggtggag 147

<210> SEQ ID NO 5
<211> LENGTH: 488
<212> TYPE: DNA
<213> ORGANISM: Homo sapiens

<400> SEQUENCE: 5
gtgcaatcat tggactcatg gtgggcggtg ttgtcatagc gacagtgatc gtcatcacct 60
tggtgatgct gaagaagaaa cagtacacat ccattcatca tggtgtggtg gaggttgacg 120
ccgctgtcac cccagaggag cgccacctgt ccaagatgca gcagaacggc tacgaaaatc 180
caacctacaa gttctttgag cagatgcaga actagacccc cgccacagca gcctctgaag 240
ttggacagca aaaccattgc ttcactaccc atcggtgtcc atttatagaa taatgtggga 300
agaaacaaac ccgttttatg atttactcat tatcgccttt tgacagctgt gctgtaacac 360
aagtagatgc ctgaacttga attaatccac acatcagtaa tgtattctat ctctctttac 420
attttggtct ctatactaca ttattaatgg gttttgtgta ctgtaaagaa tttagctgta 480
tcaaacta 488

<210> SEQ ID NO 6
<211> LENGTH: 460
<212> TYPE: DNA
<213> ORGANISM: Homo sapiens

<400> SEQUENCE: 6
gtgttctttg cagaagatgt gggttcaaac aaaggtgcaa tcattggact catggtgggc 60
ggtgttgtca tagcgacagt gatcgtcatc accttggtga tgctgaagaa gaaacagtac 120
acatccattc atcatggtgt ggtggaggtt gacgccgctg tcaccccaga ggagcgccac 180
ctgtccaaga tgcagcagaa cggctacgaa aatccaacct acaagttctt tgagcagatg 240
cagaactaga cccccgccac agcagcctct gaagttggac agcaaaacca ttgcttcact 300
acccatcggt gtccatttat agaataatgt gggaagaaac aaacccgttt tatgatttac 360
tcattatcgc cttttgacag ctgtgctgta acacaagtag atgcctgaac ttgaattaat 420
ccacacatca gtaatgtatt ctatctctct ttacattttg 460

<210> SEQ ID NO 7
<211> LENGTH: 531
<212> TYPE: DNA
<213> ORGANISM: Homo sapiens

<400> SEQUENCE: 7
gttctgggtt gacaaatatc aagacggagg agatctctga agtgaagatg gatgcagaat 60
tccgacatga ctcaggatat gaagttcatc atcaaaaatt ggtgttcttt gcagaagatg 120
tgggttcaaa caaaggtgca atcattggac tcatggtggg cggtgttgtc atagcgacag 180
tgatcgtcat caccttggtg atgctgaaga agaaacagta cacatccatt catcatggtg 240
tggtggaggt tgacgccgct gtcaccccag aggagcgcca cctgtccaag atgcagcaga 300
acggctacga aaatccaacc tacaagttct ttgagcagat gcagaactag acccccgcca 360
cagcagcctc tgaagttgga cagcaaaacc attgcttcac tacccatcgg tgtccattta 420
tagaataatg tgggaagaaa caaacccgtt ttatgattta ctcattatcg ccttttgaca 480
gctgtgctgt aacacaagta gatgcctgaa cttgaattaa tccacacatc a 531

<210> SEQ ID NO 8
<211> LENGTH: 450
<212> TYPE: DNA
<213> ORGANISM: Homo sapiens

<400> SEQUENCE: 8
atggatgcag aattccgaca tgactcagga tatgaagttc atcatcaaaa attggtgttc 60
tttgcagaag atgtgggttc aaacaaaggt gcaatcattg gactcatggt gggcggtgtt 120
gtcatagcga cagtgatcgt catcaccttg gtgatgctga agaagaaaca gtacacatcc 180
attcatcatg gtgtggtgga ggttgacgcc gctgtcaccc cagaggagcg ccacctgtcc 240
aagatgcagc agaacggcta cgaaaatcca acctacaagt tctttgagca gatgcagaac 300
tagacccccg ccacagcagc ctctgaagtt ggacagcaaa accattgctt cactacccat 360
cggtgtccat ttatagaata atgtgggaag aaacaaaccc gttttatgat ttactcatta 420
tcgccttttg acagctgtgc tgtaacacaa 450

<210> SEQ ID NO 9
<211> LENGTH: 626
<212> TYPE: DNA
<213> ORGANISM: Homo sapiens

<400> SEQUENCE: 9
agttcagcct ggacgatctc cagccgtggc attcttttgg ggctgactct gtgccagcca 60
acacagaaaa cgaagttgag cctgttgatg cccgccctgc tgccgaccga ggactgacca 120
ctcgaccagg ttctgggttg acaaatatca agacggagga gatctctgaa gtgaagatgg 180
atgcagaatt ccgacatgac tcaggatatg aagttcatca tcaaaaattg gtgttctttg 240
cagaagatgt gggttcaaac aaaggtgcaa tcattggact catggtgggc ggtgttgtca 300
tagcgacagt gatcgtcatc accttggtga tgctgaagaa gaaacagtac acatccattc 360
atcatggtgt ggtggaggtt gacgccgctg tcaccccaga ggagcgccac ctgtccaaga 420
tgcagcagaa cggctacgaa aatccaacct acaagttctt tgagcagatg cagaactaga 480
cccccgccac agcagcctct gaagttggac agcaaaacca ttgcttcact acccatcggt 540
gtccatttat agaataatgt gggaagaaac aaacccgttt tatgatttac tcattatcgc 600
cttttgacag ctgtgctgta acacaa 626

<210> SEQ ID NO 10
<211> LENGTH: 348
<212> TYPE: DNA
<213> ORGANISM: Homo sapiens

<400> SEQUENCE: 10
gtgcaatcat tggactcatg gtgggcggtg ttgtcatagc gacagtgatc gtcatcacct 60
tggtgatgct gaagaagaaa cagtacacat ccattcatca tggtgtggtg gaggttgacg 120
ccgctgtcac cccagaggag cgccacctgt ccaagatgca gcagaacggc tacgaaaatc 180
caacctacaa gttctttgag cagatgcaga actagacccc cgccacagca gcctctgaag 240
ttggacagca aaaccattgc ttcactaccc atcggtgtcc atttatagaa taatgtggga 300
agaaacaaac ccgttttatg atttactcat tatcgccttt tgacagct 348

<210> SEQ ID NO 11
<211> LENGTH: 274
<212> TYPE: DNA
<213> ORGANISM: Homo sapiens

<400> SEQUENCE: 11
gtgcaatcat tggactcatg gtgggcggtg ttgtcatagc gacagtgatc gtcatcacct 60
tggtgatgct gaagaagaaa cagtacacat ccattcatca tggtgtggtg gaggttgacg 120
ccgctgtcac cccagaggag cgccacctgt ccaagatgca gcagaacggc tacgaaaatc 180
caacctacaa gttctttgag cagatgcaga actagacccc cgccacagca gcctctgaag 240
ttggacagca aaaccattgc ttcactaccc atcg 274

<210> SEQ ID NO 12
<211> LENGTH: 308
<212> TYPE: DNA
<213> ORGANISM: Homo sapiens

<400> SEQUENCE: 12
gtgttctttg cagaagatgt gggttcaaac aaaggtgcaa tcattggact catggtgggc 60
ggtgttgtca tagcgacagt gatcgtcatc accttggtga tgctgaagaa gaaacagtac 120
acatccattc atcatggtgt ggtggaggtt gacgccgctg tcaccccaga ggagcgccac 180
ctgtccaaga tgcagcagaa cggctacgaa aatccaacct acaagttctt tgagcagatg 240
cagaactaga cccccgccac agcagcctct gaagttggac agcaaaacca ttgcttcact 300
acccatcg 308

<210> SEQ ID NO 13
<211> LENGTH: 211
<212> TYPE: DNA
<213> ORGANISM: Homo sapiens

<400> SEQUENCE: 13
aagatgtggg ttcaaacaaa ggtgcaatca ttggactcat ggtgggcggt gttgtcatag 60
cgacagtgat cgtcatcacc ttggtgatgc tgaagaagaa acagtacaca tccattcatc 120
atggtgtggt ggaggttgac gccgctgtca ccccagagga gcgccacctg tccaagatgc 180
agcagaacgg ctacgaaaat ccaacctaca a 211

<210> SEQ ID NO 14
<211> LENGTH: 325
<212> TYPE: DNA
<213> ORGANISM: Homo sapiens

<400> SEQUENCE: 14
gttctgggtt gacaaatatc aagacggagg agatctctga agtgaagatg gatgcagaat 60
tccgacatga ctcaggatat gaagttcatc atcaaaaatt ggtgttcttt gcagaagatg 120
tgggttcaaa caaaggtgca atcattggac tcatggtggg cggtgttgtc atagcgacag 180
tgatcgtcat caccttggtg atgctgaaga agaaacagta cacatccatt catcatggtg 240
tggtggaggt tgacgccgct gtcaccccag aggagcgcca cctgtccaag atgcagcaga 300
acggctacga aaatccaacc tacaa 325

<210> SEQ ID NO 15
<211> LENGTH: 214
<212> TYPE: DNA
<213> ORGANISM: Homo sapiens

<400> SEQUENCE: 15
acggaggaga tctctgaagt gaagatggat gcagaattcc gacatgactc aggatatgaa 60
gttcatcatc aaaaattggt gttctttgca gaagatgtgg gttcaaacaa aggtgcaatc 120
attggactca tggtgggcgg tgttgtcata gcgacagtga tcgtcatcac cttggtgatg 180
ctgaagaaga aacagtacac atccattcat catg 214

<210> SEQ ID NO 16
<211> LENGTH: 82
<212> TYPE: DNA
<213> ORGANISM: Homo sapiens

<400> SEQUENCE: 16
gtgcaatcat tggactcatg gtgggcggtg ttgtcatagc gacagtgatc gtcatcacct 60
tggtgatgct gaagaagaaa ca 82

<210> SEQ ID NO 17
<211> LENGTH: 170
<212> TYPE: DNA
<213> ORGANISM: Homo sapiens

<400> SEQUENCE: 17
atggatgcag aattccgaca tgactcagga tatgaagttc atcatcaaaa attggtgttc 60
tttgcagaag atgtgggttc aaacaaaggt gcaatcattg gactcatggt gggcggtgtt 120
gtcatagcga cagtgatcgt catcaccttg gtgatgctga agaagaaaca 170

<210> SEQ ID NO 18
<211> LENGTH: 17
<212> TYPE: PRT
<213> ORGANISM: Homo sapiens

<400> SEQUENCE: 18

Met Ser Cys Phe Arg Lys Ser Lys Thr Ile Gln Met Thr Ser Trp Pro
1 5 10 15

Thr

<210> SEQ ID NO 19
<211> LENGTH: 13
<212> TYPE: PRT
<213> ORGANISM: Homo sapiens

<400> SEQUENCE: 19

Leu Ser Leu Leu Met Pro Ala Leu Leu Pro Thr Glu Asp
1 5 10

<210> SEQ ID NO 20
<211> LENGTH: 7
<212> TYPE: PRT
<213> ORGANISM: Homo sapiens

<400> SEQUENCE: 20

Gly Val Val Glu Val Leu Gly
1 5

<210> SEQ ID NO 21
<211> LENGTH: 15
<212> TYPE: PRT
<213> ORGANISM: Homo sapiens

<400> SEQUENCE: 21

Met Ile Tyr Ser Leu Ser Pro Phe Asp Ser Cys Ala Val Thr Gln
1 5 10 15

<210> SEQ ID NO 22
<211> LENGTH: 11
<212> TYPE: PRT
<213> ORGANISM: Homo sapiens

<400> SEQUENCE: 22

Trp Val Asp Lys Tyr Gln Asp Gly Gly Asp Leu
1 5 10

<210> SEQ ID NO 23
<211> LENGTH: 41
<212> TYPE: PRT

<213> ORGANISM: Homo sapiens

<400> SEQUENCE: 23

Trp Met Gln Asn Ser Asp Met Thr Gln Asp Met Lys Phe Ile Ile Lys
1 5 10 15

Asn Trp Cys Ser Leu Gln Lys Met Trp Val Gln Thr Lys Val Gln Ser
20 25 30

Leu Asp Ser Trp Trp Ala Val Leu Ser
35 40

<210> SEQ ID NO 24
<211> LENGTH: 175
<212> TYPE: PRT
<213> ORGANISM: Homo sapiens

<400> SEQUENCE: 24

Met Ile Ser Glu Pro Arg Ile Ser Tyr Gly Asn Asp Ala Leu Met Pro
1 5 10 15

Ser Leu Thr Glu Thr Lys Thr Thr Val Glu Leu Leu Pro Val Asn Gly
20 25 30

Glu Phe Ser Leu Asp Asp Leu Gln Pro Trp His Ser Phe Gly Ala Asp
35 40 45

Ser Val Pro Ala Asn Thr Glu Asn Glu Val Glu Pro Val Asp Ala Arg
50 55 60

Pro Ala Ala Asp Arg Gly Leu Thr Thr Arg Pro Gly Ser Gly Leu Thr
65 70 75 80

Asn Ile Lys Thr Glu Glu Ile Ser Glu Val Lys Met Asp Ala Glu Phe
85 90 95

Arg His Asp Ser Gly Tyr Glu Val His His Gln Lys Leu Val Phe Phe
100 105 110

Ala Glu Asp Val Gly Ser Asn Lys Gly Ala Ile Ile Gly Leu Met Val
115 120 125

Gly Gly Val Val Ile Ala Thr Val Ile Val Ile Thr Leu Val Met Leu
130 135 140

Lys Lys Lys Gln Tyr Thr Ser Ile His His Gly Val Val Glu Met Ser
145 150 155 160

Cys Phe Arg Lys Ser Lys Thr Ile Gln Met Thr Ser Trp Pro Thr
165 170 175

<210> SEQ ID NO 25
<211> LENGTH: 80
<212> TYPE: PRT
<213> ORGANISM: Homo sapiens

<400> SEQUENCE: 25

Met Asp Ala Glu Phe Arg His Asp Ser Gly Tyr Glu Val His His Gln
1 5 10 15

Lys Leu Val Phe Phe Ala Glu Asp Val Gly Ser Asn Lys Gly Ala Ile
20 25 30

Ile Gly Leu Met Val Gly Gly Val Val Ile Ala Thr Val Ile Val Ile
35 40 45

Thr Leu Val Met Leu Lys Lys Lys Gln Tyr Thr Ser Ile His His Gly
50 55 60

Val Val Glu Leu Ser Leu Leu Met Pro Ala Leu Leu Pro Thr Glu Asp
65 70 75 80

<210> SEQ ID NO 26

<211> LENGTH: 70
<212> TYPE: PRT
<213> ORGANISM: Homo sapiens

<400> SEQUENCE: 26

```
Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Tyr Thr Ser Ile His His Gly
    50                  55                  60

Val Val Glu Val Leu Gly
65                  70
```

<210> SEQ ID NO 27
<211> LENGTH: 49
<212> TYPE: PRT
<213> ORGANISM: Homo sapiens

<400> SEQUENCE: 27

```
Met Val Gly Gly Val Val Ile Ala Thr Val Ile Val Ile Thr Leu Val
1               5                   10                  15

Met Leu Lys Lys Lys Gln Tyr Thr Ser Ile His His Gly Val Val Glu
            20                  25                  30

Val Phe Phe Ala Glu Asp Val Gly Ser Asn Lys Gly Ala Ile Ile Gly
        35                  40                  45

Leu
```

<210> SEQ ID NO 28
<211> LENGTH: 65
<212> TYPE: PRT
<213> ORGANISM: Homo sapiens

<400> SEQUENCE: 28

```
Met Val Gly Gly Val Val Ile Ala Thr Val Ile Val Ile Thr Leu Val
1               5                   10                  15

Met Leu Lys Lys Lys Gln Tyr Thr Ser Ile His His Gly Val Val Glu
            20                  25                  30

Val Asp Ala Ala Val Thr Pro Glu Glu Arg His Leu Ser Lys Met Gln
        35                  40                  45

Gln Asn Gly Tyr Glu Asn Pro Thr Tyr Lys Phe Phe Glu Gln Met Gln
    50                  55                  60

Asn
65
```

<210> SEQ ID NO 29
<211> LENGTH: 102
<212> TYPE: PRT
<213> ORGANISM: Homo sapiens

<400> SEQUENCE: 29

```
Met Pro Glu Leu Glu Leu Ile His Thr Ser Val Met Tyr Ser Ile Ser
1               5                   10                  15

Leu Tyr Ile Leu Val Phe Phe Ala Glu Asp Val Gly Ser Asn Lys Gly
            20                  25                  30

Ala Ile Ile Gly Leu Met Val Gly Gly Val Val Ile Ala Thr Val Ile
        35                  40                  45
```

Val Ile Thr Leu Val Met Leu Lys Lys Lys Gln Tyr Thr Ser Ile His
50 55 60

His Gly Val Val Glu Val Asp Ala Ala Val Thr Pro Glu Glu Arg His
65 70 75 80

Leu Ser Lys Met Gln Gln Asn Gly Tyr Glu Asn Pro Thr Tyr Lys Phe
85 90 95

Phe Glu Gln Met Gln Asn
100

<210> SEQ ID NO 30
<211> LENGTH: 100
<212> TYPE: PRT
<213> ORGANISM: Homo sapiens

<400> SEQUENCE: 30

Met Asp Ala Glu Phe Arg His Asp Ser Gly Tyr Glu Val His His Gln
1 5 10 15

Lys Leu Val Phe Phe Ala Glu Asp Val Gly Ser Asn Lys Gly Ala Ile
20 25 30

Ile Gly Leu Met Val Gly Gly Val Val Ile Ala Thr Val Ile Val Ile
35 40 45

Thr Leu Val Met Leu Lys Lys Lys Gln Tyr Thr Ser Ile His His Gly
50 55 60

Val Val Glu Val Asp Ala Ala Val Thr Pro Glu Glu Arg His Leu Ser
65 70 75 80

Lys Met Gln Gln Asn Gly Tyr Glu Asn Pro Thr Tyr Lys Phe Phe Glu
85 90 95

Gln Met Gln Asn
100

<210> SEQ ID NO 31
<211> LENGTH: 115
<212> TYPE: PRT
<213> ORGANISM: Homo sapiens

<400> SEQUENCE: 31

Met Ile Tyr Ser Leu Ser Pro Phe Asp Ser Cys Ala Val Thr Gln Met
1 5 10 15

Asp Ala Glu Phe Arg His Asp Ser Gly Tyr Glu Val His His Gln Lys
20 25 30

Leu Val Phe Phe Ala Glu Asp Val Gly Ser Asn Lys Gly Ala Ile Ile
35 40 45

Gly Leu Met Val Gly Gly Val Val Ile Ala Thr Val Ile Val Ile Thr
50 55 60

Leu Val Met Leu Lys Lys Lys Gln Tyr Thr Ser Ile His His Gly Val
65 70 75 80

Val Glu Val Asp Ala Ala Val Thr Pro Glu Glu Arg His Leu Ser Lys
85 90 95

Met Gln Gln Asn Gly Tyr Glu Asn Pro Thr Tyr Lys Phe Phe Glu Gln
100 105 110

Met Gln Asn
115

<210> SEQ ID NO 32
<211> LENGTH: 100
<212> TYPE: PRT
<213> ORGANISM: Homo sapiens

<400> SEQUENCE: 32

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Tyr Thr Ser Ile His His Gly
    50                  55                  60

Val Val Glu Val Asp Ala Ala Val Thr Pro Glu Glu Arg His Leu Ser
65                  70                  75                  80

Lys Met Gln Gln Asn Gly Tyr Glu Asn Pro Thr Tyr Lys Phe Phe Glu
                85                  90                  95

Gln Met Gln Asn
            100

<210> SEQ ID NO 33
<211> LENGTH: 81
<212> TYPE: PRT
<213> ORGANISM: Homo sapiens

<400> SEQUENCE: 33

Met Ile Tyr Ser Leu Ser Pro Phe Asp Ser Cys Ala Ile Ile Gly Leu
1               5                   10                  15

Met Val Gly Gly Val Val Ile Ala Thr Val Ile Val Ile Thr Leu Val
            20                  25                  30

Met Leu Lys Lys Lys Gln Tyr Thr Ser Ile His His Gly Val Val Glu
        35                  40                  45

Val Asp Ala Ala Val Thr Pro Glu Glu Arg His Leu Ser Lys Met Gln
    50                  55                  60

Gln Asn Gly Tyr Glu Asn Pro Thr Tyr Lys Phe Phe Glu Gln Met Gln
65                  70                  75                  80

Asn

<210> SEQ ID NO 34
<211> LENGTH: 129
<212> TYPE: PRT
<213> ORGANISM: Homo sapiens

<400> SEQUENCE: 34

Met Val Trp Trp Arg Leu Thr Pro Leu Ser Pro Gln Arg Ser Ala Thr
1               5                   10                  15

Cys Pro Arg Cys Ser Arg Thr Ala Thr Lys Ile Gln Pro Thr Ser Ser
            20                  25                  30

Leu Ser Arg Cys Arg Thr Arg Pro Pro Pro Gln Gln Pro Leu Lys Leu
        35                  40                  45

Asp Ser Lys Thr Ile Ala Ser Leu Pro Ile Gly Ala Ile Ile Gly Leu
    50                  55                  60

Met Val Gly Gly Val Val Ile Ala Thr Val Ile Val Ile Thr Leu Val
65                  70                  75                  80

Met Leu Lys Lys Lys Gln Tyr Thr Ser Ile His His Gly Val Val Glu
                85                  90                  95

Val Asp Ala Ala Val Thr Pro Glu Glu Arg His Leu Ser Lys Met Gln
            100                 105                 110

Gln Asn Gly Tyr Glu Asn Pro Thr Tyr Lys Phe Phe Glu Gln Met Gln 115 120 125

Asn

<210> SEQ ID NO 35
<211> LENGTH: 65
<212> TYPE: PRT
<213> ORGANISM: Homo sapiens

<400> SEQUENCE: 35

Met Val Gly Gly Val Val Ile Ala Thr Val Ile Val Ile Thr Leu Val
1 5 10 15

Met Leu Lys Lys Lys Gln Tyr Thr Ser Ile His His Gly Val Val Glu
20 25 30

Val Asp Ala Ala Val Thr Pro Glu Glu Arg His Leu Ser Lys Met Gln
35 40 45

Gln Asn Gly Tyr Glu Asn Pro Thr Tyr Lys Phe Phe Glu Gln Met Gln
50 55 60

Asn
65

<210> SEQ ID NO 36
<211> LENGTH: 103
<212> TYPE: PRT
<213> ORGANISM: Homo sapiens

<400> SEQUENCE: 36

Met Val Gly Gly Val Val Ile Ala Thr Val Ile Val Ile Thr Leu Val
1 5 10 15

Met Leu Lys Lys Lys Gln Tyr Thr Ser Ile His His Gly Val Val Glu
20 25 30

Val Asp Ala Ala Val Thr Pro Glu Glu Arg His Leu Ser Lys Met Gln
35 40 45

Gln Asn Gly Tyr Glu Asn Pro Thr Tyr Lys Arg Cys Gly Phe Lys Gln
50 55 60

Arg Cys Asn His Trp Thr His Gly Gly Arg Cys Cys His Ser Asp Ser
65 70 75 80

Asp Arg His His Leu Gly Asp Ala Glu Glu Glu Thr Val His Ile His
85 90 95

Ser Ser Trp Cys Gly Gly Gly
100

<210> SEQ ID NO 37
<211> LENGTH: 105
<212> TYPE: PRT
<213> ORGANISM: Homo sapiens

<400> SEQUENCE: 37

Met Asp Ala Glu Phe Arg His Asp Ser Gly Tyr Glu Val His His Gln
1 5 10 15

Lys Leu Val Phe Phe Ala Glu Asp Val Gly Ser Asn Lys Gly Ala Ile
20 25 30

Ile Gly Leu Met Val Gly Gly Val Val Ile Ala Thr Val Ile Val Ile
35 40 45

Thr Leu Val Met Leu Lys Lys Lys Gln Tyr Thr Ser Ile His His Gly
50 55 60

Val Val Glu Val Asp Ala Ala Val Thr Pro Glu Glu Arg His Leu Ser
65 70 75 80

```
Lys Met Gln Gln Asn Gly Tyr Glu Asn Pro Thr Tyr Lys Phe Trp Val
                85                  90                  95

Asp Lys Tyr Gln Asp Gly Gly Asp Leu
            100                 105


<210> SEQ ID NO 38
<211> LENGTH: 68
<212> TYPE: PRT
<213> ORGANISM: Homo sapiens

<400> SEQUENCE: 38

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Tyr Thr Ser Ile His His Asp
    50                  55                  60

Gly Gly Asp Leu
65


<210> SEQ ID NO 39
<211> LENGTH: 61
<212> TYPE: PRT
<213> ORGANISM: Homo sapiens

<400> SEQUENCE: 39

Met Val Gly Gly Val Val Ile Ala Thr Val Ile Val Ile Thr Leu Val
1               5                   10                  15

Met Leu Lys Lys Lys Gln Cys Asn His Trp Thr His Gly Gly Arg Cys
            20                  25                  30

Cys His Ser Asp Ser Asp Arg His His Leu Gly Asp Ala Glu Glu Glu
        35                  40                  45

Thr Val Gln Ser Leu Asp Ser Trp Trp Ala Val Leu Ser
    50                  55                  60


<210> SEQ ID NO 40
<211> LENGTH: 98
<212> TYPE: PRT
<213> ORGANISM: Homo sapiens

<400> SEQUENCE: 40

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Trp Met Gln Asn Ser Asp Met
    50                  55                  60

Thr Gln Asp Met Lys Phe Ile Ile Lys Asn Trp Cys Ser Leu Gln Lys
65                  70                  75                  80

Met Trp Val Gln Thr Lys Val Gln Ser Leu Asp Ser Trp Trp Ala Val
                85                  90                  95

Leu Ser


<210> SEQ ID NO 41
```

<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 41
aagcagctca tctccaccac ac 22

<210> SEQ ID NO 42
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 42
aacaggctca actccaccac ac 22

<210> SEQ ID NO 43
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 43
caacccagaa cctccaccac ac 22

<210> SEQ ID NO 44
<211> LENGTH: 21
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(21)
<223> OTHER INFORMATION: SYNTHETIC

<400> SEQUENCE: 44
gcaaagaaca cctccaccac a 21

<210> SEQ ID NO 45
<211> LENGTH: 26
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(26)
<223> OTHER INFORMATION: SYNTHETIC

<400> SEQUENCE: 45
ccaatgattg cactagtttg atacag 26

<210> SEQ ID NO 46
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 46
tgcaaagaac accaaaatgt aaag 24

<210> SEQ ID NO 47
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 47
caacccagaa ctgatgtgtg ga 22

<210> SEQ ID NO 48
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 48
tctgcatcca tttgtgttac ag 22

<210> SEQ ID NO 49
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 49
caggctgaac tttgtgttac ag 22

<210> SEQ ID NO 50
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 50
caatgattgc acagctgtca aaag 24

<210> SEQ ID NO 51
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 51
caatgattgc accgatgggt agtg 24

<210> SEQ ID NO 52
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 52
gcaaagaaca ccgatgggta gt 22

<210> SEQ ID NO 53
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 53
acccacatct tttgtaggtt gg 22

<210> SEQ ID NO 54
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 54
caacccagaa cttgtaggtt gg 22

<210> SEQ ID NO 55
<211> LENGTH: 22
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(22)
<223> OTHER INFORMATION: SYNTHETIC

<400> SEQUENCE: 55
atctcctccg tcatgatgaa tg 22

<210> SEQ ID NO 56
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 56
caatgattgc actgtttctt cttc 24

<210> SEQ ID NO 57
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 57
ttctgcatcc attgtttctt cttc 24

<210> SEQ ID NO 58
<211> LENGTH: 36
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(36)
<223> OTHER INFORMATION: SYNTHETIC

<400> SEQUENCE: 58
atataggatc cgtgatcgtc atcaccttgg tgatgc 36

<210> SEQ ID NO 59
<211> LENGTH: 35
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(35)
<223> OTHER INFORMATION: SYNTHETIC

<400> SEQUENCE: 59
tatatctcga gcaccatgag tccaatgatt gcacc 35

<210> SEQ ID NO 60
<211> LENGTH: 60
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(60)
<223> OTHER INFORMATION: SYNTHETIC

<400> SEQUENCE: 60
cccaccatga gtccaatgat tgcacctttg tttgaaccca catcttctgc aaagaacacc 60

<210> SEQ ID NO 61
<211> LENGTH: 15
<212> TYPE: PRT
<213> ORGANISM: Artificial Sequence
<220> FEATURE:
<223> OTHER INFORMATION: SYNTHETIC
<220> FEATURE:
<221> NAME/KEY: MOD_RES
<222> LOCATION: (1)..(15)
<223> OTHER INFORMATION: SYNTHETIC

<400> SEQUENCE: 61

Cys Phe Arg Lys Ser Lys Thr Ile Gln Met Thr Ser Trp Pro Thr
1 5 10 15

<210> SEQ ID NO 62
<211> LENGTH: 21
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(21)
<223> OTHER INFORMATION: SYNTHETIC

<400> SEQUENCE: 62
gtcatagcga cagtgatcgt c 21

<210> SEQ ID NO 63
<211> LENGTH: 23
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(23)
<223> OTHER INFORMATION: SYNTHETIC

<400> SEQUENCE: 63
cttggttcac taatcatgtt ggc 23

<210> SEQ ID NO 64
<211> LENGTH: 20
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(20)
<223> OTHER INFORMATION: SYNTHETIC

<400> SEQUENCE: 64
tttgtgattc cctaccgctg 20

<210> SEQ ID NO 65
<211> LENGTH: 21
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(21)
<223> OTHER INFORMATION: SYNTHETIC

<400> SEQUENCE: 65
tgccagtgaa gatgagtttc g 21

<210> SEQ ID NO 66
<211> LENGTH: 20
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(20)
<223> OTHER INFORMATION: SYNTHETIC

<400> SEQUENCE: 66
accttctaca atgagctgcg 20

<210> SEQ ID NO 67
<211> LENGTH: 21
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(21)
<223> OTHER INFORMATION: SYNTHETIC

<400> SEQUENCE: 67
cctggatagc aacgtacatg g 21

<210> SEQ ID NO 68
<211> LENGTH: 20
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(20)
<223> OTHER INFORMATION: SYNTHETIC

<400> SEQUENCE: 68
ctggatggct acgtacatgg 20

<210> SEQ ID NO 69
<211> LENGTH: 20
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(20)
<223> OTHER INFORMATION: SYNTHETIC

<400> SEQUENCE: 69
tcgtgcgtga cattaaggag 20

<210> SEQ ID NO 70
<211> LENGTH: 20
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(20)
<223> OTHER INFORMATION: SYNTHETIC

<400> SEQUENCE: 70
ttgccaatgg tgatgacctg 20

<210> SEQ ID NO 71
<211> LENGTH: 34
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(34)
<223> OTHER INFORMATION: SYNTHETIC

<400> SEQUENCE: 71
aattaaggat ccatgggaat tcacgtgatt ctcc 34

<210> SEQ ID NO 72
<211> LENGTH: 40
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(40)
<223> OTHER INFORMATION: SYNTHETIC

<400> SEQUENCE: 72
ttaattctcg agctactaga aaacacagct aacagaatgc 40

<210> SEQ ID NO 73
<211> LENGTH: 37
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(37)
<223> OTHER INFORMATION: SYNTHETIC

<400> SEQUENCE: 73
aattaaggat ccaacgttaa ccctgtaatg aatactg 37

<210> SEQ ID NO 74
<211> LENGTH: 38
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(38)
<223> OTHER INFORMATION: SYNTHETIC

<400> SEQUENCE: 74
actttgctcg agctcatcaa catgacacag tagacatg 38

<210> SEQ ID NO 75
<211> LENGTH: 40
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(40)

<223> OTHER INFORMATION: SYNTHETIC

<400> SEQUENCE: 75
atgagctcga gcaaagtgat tttccacaca gtattatcac 40

<210> SEQ ID NO 76
<211> LENGTH: 38
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(38)
<223> OTHER INFORMATION: SYNTHETIC

<400> SEQUENCE: 76
ttaattcccg ggcaacgtta accctgtaat gaatactg 38

<210> SEQ ID NO 77
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 77
atgtccaata tgaccgccat gttg 24

<210> SEQ ID NO 78
<211> LENGTH: 57
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(57)
<223> OTHER INFORMATION: SYNTHETIC

<400> SEQUENCE: 78
aacgttggat ccagtcgacc tatagtgagt cgtattaagt actctagcct taagagc 57

<210> SEQ ID NO 79
<211> LENGTH: 29
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(29)
<223> OTHER INFORMATION: SYNTHETIC

<400> SEQUENCE: 79
ctataggtcg actggatcca acgttaacc 29

<210> SEQ ID NO 80
<211> LENGTH: 68
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature

<222> LOCATION: (1)..(68)
<223> OTHER INFORMATION: SYNTHETIC

<400> SEQUENCE: 80
tctagaccgc ggccgcgata tcgctagcag atcttctcat ctgaaaaaca aacagaatac 60
aacctcag 68

<210> SEQ ID NO 81
<211> LENGTH: 62
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(62)
<223> OTHER INFORMATION: SYNTHETIC

<400> SEQUENCE: 81
agatctgcta gcgatatcgc ggccgcggtc tagacttcag gtaataatcc atgcaccgtc 60
tc 62

<210> SEQ ID NO 82
<211> LENGTH: 25
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(25)
<223> OTHER INFORMATION: SYNTHETIC

<400> SEQUENCE: 82
cactttgctc gagctcatca acatg 25

<210> SEQ ID NO 83
<211> LENGTH: 24
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(24)
<223> OTHER INFORMATION: SYNTHETIC

<400> SEQUENCE: 83
gtcgactgga tccaacgtta accc 24

<210> SEQ ID NO 84
<211> LENGTH: 42
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(42)
<223> OTHER INFORMATION: SYNTHETIC

<400> SEQUENCE: 84
gctgtcgtgg gaactgaaaa acaaacagaa tacaacctca gc 42

<210> SEQ ID NO 85
<211> LENGTH: 39
<212> TYPE: DNA

<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(39)
<223> OTHER INFORMATION: SYNTHETIC

<400> SEQUENCE: 85
tcaagatgaa gtcggtaata atccatgcac cgtctcacc 39

<210> SEQ ID NO 86
<211> LENGTH: 40
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(40)
<223> OTHER INFORMATION: SYNTHETIC

<400> SEQUENCE: 86
gtttgttttt cagatgagct gcttcagaaa gagcaaaact 40

<210> SEQ ID NO 87
<211> LENGTH: 37
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(37)
<223> OTHER INFORMATION: SYNTHETIC

<400> SEQUENCE: 87
gcatggatta ttacctccac cacaccatga tgaatgg 37

<210> SEQ ID NO 88
<211> LENGTH: 43
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(43)
<223> OTHER INFORMATION: SYNTHETIC

<400> SEQUENCE: 88
ctgaagcagc tcatctgaaa aacaaacaga atacaacctc agc 43

<210> SEQ ID NO 89
<211> LENGTH: 37
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(37)
<223> OTHER INFORMATION: SYNTHETIC

<400> SEQUENCE: 89
ggtgtggtgg aggtaataat ccatgcaccg tctcacc 37

<210> SEQ ID NO 90
<211> LENGTH: 24

<212> TYPE: PRT
<213> ORGANISM: Artificial Sequence
<220> FEATURE:
<223> OTHER INFORMATION: SYNTHETIC
<220> FEATURE:
<221> NAME/KEY: MOD_RES
<222> LOCATION: (1)..(24)
<223> OTHER INFORMATION: SYNTHETIC

<400> SEQUENCE: 90

```
Thr Val Ile Val Ile Thr Leu Val Met Leu Lys Lys Lys Gln Tyr Thr
1               5                   10                  15

Ser Ile His His Gly Val Val Glu
            20
```

<210> SEQ ID NO 91
<211> LENGTH: 12
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(12)
<223> OTHER INFORMATION: SYNTHETIC

<400> SEQUENCE: 91

```
gctcatctcc ac                                                          12
```

<210> SEQ ID NO 92
<211> LENGTH: 175
<212> TYPE: PRT
<213> ORGANISM: Artificial Sequence
<220> FEATURE:
<223> OTHER INFORMATION: SYNTHETIC
<220> FEATURE:
<221> NAME/KEY: MOD_RES
<222> LOCATION: (1)..(175)
<223> OTHER INFORMATION: SYNTHETIC

<400> SEQUENCE: 92

```
Met Ile Ser Glu Pro Arg Ile Ser Tyr Gly Asn Asp Ala Leu Met Pro
1               5                   10                  15

Ser Leu Thr Glu Thr Lys Thr Thr Val Glu Leu Leu Pro Val Asn Gly
            20                  25                  30

Glu Phe Ser Leu Asp Asp Leu Gln Pro Trp His Ser Phe Gly Ala Asp
        35                  40                  45

Ser Val Pro Ala Asn Thr Glu Asn Glu Val Glu Pro Val Asp Ala Arg
    50                  55                  60

Pro Ala Ala Asp Arg Gly Leu Thr Thr Arg Pro Gly Ser Gly Leu Thr
65                  70                  75                  80

Asn Ile Lys Thr Glu Glu Ile Ser Glu Val Lys Met Asp Ala Glu Phe
                85                  90                  95

Arg His Asp Ser Gly Tyr Glu Val His His Gln Lys Leu Val Phe Phe
            100                 105                 110

Ala Glu Asp Val Gly Ser Asn Lys Gly Ala Ile Ile Gly Leu Met Val
        115                 120                 125

Gly Gly Val Val Ile Ala Thr Val Ile Val Ile Thr Leu Val Met Leu
    130                 135                 140

Lys Lys Lys Gln Tyr Thr Ser Ile His His Gly Val Val Glu Met Ser
145                 150                 155                 160

Cys Phe Arg Lys Ser Lys Thr Ile Gln Met Thr Ser Trp Pro Thr
                165                 170                 175
```

<210> SEQ ID NO 93
<211> LENGTH: 11
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(11)
<223> OTHER INFORMATION: SYNTHETIC

<400> SEQUENCE: 93
aagcagctca t 11

<210> SEQ ID NO 94
<211> LENGTH: 11
<212> TYPE: DNA
<213> ORGANISM: Artificial Sequence
<220> FEATURE:
<223> OTHER INFORMATION: SYNTHETIC
<220> FEATURE:
<221> NAME/KEY: misc_feature
<222> LOCATION: (1)..(11)
<223> OTHER INFORMATION: SYNTHETIC

<400> SEQUENCE: 94
ctccaccaca c 11

<210> SEQ ID NO 95
<211> LENGTH: 695
<212> TYPE: PRT
<213> ORGANISM: Artificial Sequence
<220> FEATURE:
<223> OTHER INFORMATION: SYNTHETIC

<400> SEQUENCE: 95

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

-continued

```
Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
```

-continued

```
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695


<210> SEQ ID NO 96
<211> LENGTH: 11
<212> TYPE: PRT
<213> ORGANISM: Artificial Sequence
<220> FEATURE:
<223> OTHER INFORMATION: SYNTHETIC

<400> SEQUENCE: 96

Ser Lys Thr Ile Gln Met Thr Ser Trp Pro Thr
1               5                   10


<210> SEQ ID NO 97
<211> LENGTH: 16
<212> TYPE: PRT
<213> ORGANISM: Artificial Sequence
<220> FEATURE:
<223> OTHER INFORMATION: SYNTHETIC

<400> SEQUENCE: 97

Ile Ser Tyr Gly Asn Asp Ala Leu Met Pro Ser Leu Thr Glu Thr Lys
1               5                   10                  15


<210> SEQ ID NO 98
<211> LENGTH: 9
<212> TYPE: PRT
<213> ORGANISM: Artificial Sequence
<220> FEATURE:
<223> OTHER INFORMATION: SYNTHETIC

<400> SEQUENCE: 98

Thr Ile Gln Met Thr Ser Trp Pro Thr
1               5
```